(12) United States Patent
Davis

(10) Patent No.: US 11,554,304 B1
(45) Date of Patent: Jan. 17, 2023

(54) SYSTEMS, METHODS, AND COMPUTER PROGRAM PRODUCT FOR SMART RELAY RACE TRAINING WITH RELAY BATON EXCHANGE TRACKING

(71) Applicant: Donnell A. Davis, Bowie, MD (US)

(72) Inventor: Donnell A. Davis, Bowie, MD (US)

(*) Notice: Subject to any disclaimer, the term of this patent is extended or adjusted under 35 U.S.C. 154(b) by 0 days.

(21) Appl. No.: 17/898,748

(22) Filed: Aug. 30, 2022

(51) Int. Cl.
| | | |
|---|---|---|
| *A63B 69/00* | (2006.01) | |
| *A63B 71/06* | (2006.01) | |
| *A63B 24/00* | (2006.01) | |

(52) U.S. Cl.
CPC ...... *A63B 69/0028* (2013.01); *A63B 24/0062* (2013.01); *A63B 71/0622* (2013.01); *A63B 2214/00* (2020.08); *A63B 2220/803* (2013.01); *A63B 2220/833* (2013.01); *A63B 2225/50* (2013.01)

(58) Field of Classification Search
CPC ............ A63B 24/0062; A63B 69/0028; A63B 71/0622; A63B 2214/00; A63B 2220/803; A63B 2220/833; A63B 2225/50
See application file for complete search history.

(56) References Cited

U.S. PATENT DOCUMENTS

| | | | |
|---|---|---|---|
| 9,126,094 B1 | 9/2015 | Davis | |
| 10,433,113 B2* | 10/2019 | DeAngelis | G07C 1/00 |
| 10,537,783 B2* | 1/2020 | Medina-Brodsky | A63K 3/00 |
| 10,632,395 B1 | 4/2020 | Davis | |
| 10,957,121 B2* | 3/2021 | DeAngelis | A61B 5/6825 |
| 2017/0259156 A1* | 9/2017 | DeAngelis | G07C 1/00 |
| 2017/0361198 A1* | 12/2017 | Medina-Brodsky | A63K 3/00 |
| 2019/0357009 A1* | 11/2019 | DeAngelis | A63K 1/00 |
| 2021/0236900 A1* | 8/2021 | Leedy | G09B 5/02 |

OTHER PUBLICATIONS

Seagrave, Loren, Mouchbahani, Ralph, & O'Donnell, Kevin, "Neuro-Biomechanics of Maximum Velocity Sprinting" IAAF NSA. (2009).
Carter, Shan. & Ward, Joe., "The Fastest Baton to the Finish Line" New York Times. (2012). archive.nytimes.com/www.nytimes.com/interactive/2012/07/23/sports/olympics/the-fastest-baton-to-the-finish-line.html.
Rahim, Abdur. & Shin, Jungpil. "Hand Movement Activity-Based Character Input System on a Virtual Keyboard" Electronics. (2020). doi:10.3390/electronics9050774.

* cited by examiner

*Primary Examiner* — Joshua Lee
(74) *Attorney, Agent, or Firm* — Terry M. Sanks, Esq.; Beusse Sanks, PLLC

(57) ABSTRACT

A system that includes an electronic baton device with motion and capacitive sensors. The system includes a processor and non-tangible computer readable media having stored programming instructions thereon that, when executed, cause the processor to receive sensor data from the motion and capacitive sensors, and determine an exchange zone to exchange the baton device between an incoming runner and an outgoing runner of a relay, based on the sensor data. The processor determines relay race metrics for each athlete of the relay team, baton metrics associated with each athlete, a usage efficiency in the exchange zone, and a baton transition metrics. The processor selectively displays on a display device the relay race metrics for each athlete, the determined baton metrics, the determined usage efficiency in the exchange zone, and the determined baton transition metrics in one or more selected graphical user interfaces.

20 Claims, 19 Drawing Sheets

PACE CALCULATOR

| | | |
|---|---|---|
| Time | To calculate your time, fill in your distance and pace, then click here: [Calculate Time]—1408<br><br>hours  mins  secs<br>[00]—1402  [ ]—1404  [49.1]—1406 | |
| Distance | To calculate your distance, fill in your time and pace, then click here: [Calculate Distance]—1416<br><br>[408]—1410  [Meters ▽]—1412<br>or<br>[Pick Event ▽]—1414 | |
| Pace | To calculate your pace, fill in your time and distance, then click here: [Calculate Pace]—1426<br><br>hours  mins  secs<br>[00]—1418  [00]—1420  [00.120343]—1422<br>Per [Meters ▽]—1424 | |

FIG. 14

ACCELERATION CALCULATOR

The acceleration of a moving object can be determined by using the following formula:

$$a = \frac{dv}{dt} = \frac{d^2r}{dt^2}$$

where $dv$ is the change of the velocity/speed over time $dt$ which is equal to the difference between the initial speed and the final speed of the object, the $dv$ can be found as shown below.

$dV = v1 - v0$ where v0 is the initial velocity/speed while v1 is the final velocity/speed of the moving object.

The result is 0.20563840000001 meter/square second [m/s2] — 1504

Initial Speed (v0): 18.58 — 1506   mile/hour [mph] ▽ — 1508

Final Speed (v1): 19.5 — 1510   mile/hour [mph] ▽ — 1512

The time (t): 2 — 1514   second [s] ▽ — 1516

The Acceleration (a): 0.20563840000000 — 1518   meter/square second [m/s2] ▽ — 1520

FIG. 15

SYSTEMS, METHODS, AND COMPUTER PROGRAM PRODUCT FOR SMART RELAY RACE TRAINING WITH RELAY BATON EXCHANGE TRACKING

BACKGROUND

Embodiments relate to systems, method, and computer program product for smart relay race training with relay baton exchange tracking.

Track and field differs from most other sports because it is solely measured in meters and seconds. A fraction of a second can make all the difference in track. Because of that, the technology that records data from track and field races and events must be relevant, precise, and accurate as possible. Research finds that athletes can achieve consistently better performances by applying a better understanding of high-speed running.

Developing better runners requires coaches that are willing to learn scientific principles, as well as a method of communicating knowledge to the athlete. The most known and widely used technical running model comprises three phases: the Drive, the Swing, and the Lift. A more contemporary model of high-speed running is taught through the International Association of Athletics Federations (IAAF) Coaches Education and Certification System, which emphasizes six reference points: Body Position, Recovery Mechanics, Transition Phase, Ground Preparation Phase, Ground Phase, and Arm Action. The high-speed running models generally apply to all running events, including individual athletes participating in relay events. For example, proper arm movement continues to be a challenge for both young-developing runners and advanced runners, but especially is magnified when carrying a baton. "Biomechanists have contended that the arms balance the forces of the legs to maintain the body in the proper alignment. Coaches on the other hand have promoted that the arms control the legs and thus can positively impact performance." (Seagrave, Loren et al., Neuro-Biomechanics of Maximum Velocity Sprinting, 2009).

Current training consists of time-intensive training regimens, lacks fusion of kinetic data and sports analytics, limited immediate feedback, and often apply imprecise manual calculations. For example, daily hand-off drills must be done to ensure that runners are confident in performing exchanges at full-speed. The training method is time-consuming as runners must perform multiple run-throughs to identify all variables to execute the ideal exchange zone spot usually are done in progression from half-speed, then three-quarters-speed, to full-speed, and often repeated many times as necessary per the coach's observation. Moreover, athletes and coaches are required to determine the ideal exchange zone spot for the outgoing runner to receive the baton at top speed. Savvy coaches and athletes use the formula distance=speed×time (d=s×t), then convert meters to feet in order to determine the outgoing runner's acceleration starting/static mark on the track (i.e., placement of "Go" mark). This approach requires precise variables and often is miscalculated.

BRIEF SUMMARY

Embodiments relate to systems, method, and computer program product for smart relay race training with relay baton exchange tracking.

In one aspect, a system includes an electronic baton device including motion sensors and capacitive sensors. The system also includes a processor. The system also includes non-tangible computer readable media having stored programming instructions thereon that, when executed, cause the processor to receive sensor data from the motion sensors and the capacitive sensors, determine an exchange zone to exchange the electronic baton device between an incoming runner and an outgoing runner of a relay team of athletes, based on the received sensor data, determine relay race metrics for each athlete of the relay race team of athletes, baton metrics associated with said each athlete, a usage efficiency in the exchange zone, and a baton transition metrics, and selectively display on a display device the determined relay race metrics for each athlete, the determined baton metrics associated with said each athlete, the determined usage efficiency in the exchange zone, and the determined baton transition metrics in one or more selected graphical user interfaces.

In one aspect, a computer program product includes one or more non-tangible and non-transitory computer readable media and programming instructions stored on the computer readable media, the program instructions includes program instructions to track and monitor a performance of a relay race team of athletes during a relay race as each athlete interacts with an electronic baton device, the electronic baton device includes motion sensors and capacitive sensors, program instructions to collect sensor data from the motion sensors and the capacitive sensors, program instructions to determine an exchange zone to exchange the electronic baton device between an incoming runner and an outgoing runner of a relay team of athletes, program instructions to, based on the collected sensor data, determine relay race metrics for each athlete of the relay race team of athletes, baton metrics associated with said each athlete, a usage efficiency in the exchange zone, and a baton transition metrics, and program instructions to selectively display on a display device the determined relay race metrics for each athlete, the determined baton metrics associated with said each athlete, the determined usage efficiency in the exchange zone, and the determined baton transition metrics in one or more selected graphical user interfaces.

In one aspect, a method includes by a processor tracking and monitoring performance of a relay race team of athletes during a relay race as each athlete interacts with an electronic baton device, the electronic baton device includes motion sensors and capacitive sensors, collecting sensor data from the motion sensors and the capacitive sensors, determining an exchange zone to exchange the electronic baton device between an incoming runner and an outgoing runner of a relay team of athletes, based on the sensor data, based on the collected sensor data, determining relay race metrics for each athlete of the relay race team of athletes, baton metrics associated with said each athlete, a usage efficiency in the exchange zone, and a baton transition metrics, and selectively displaying on a display device the determined relay race metrics for each athlete, the determined baton metrics associated with said each athlete, the determined usage efficiency in the exchange zone, and the determined baton transition metrics in one or more selected graphical user interfaces.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 14 illustrates a graphical user interface (GUI) of a pace calculator for an athlete in accordance with one embodiment;

FIG. 15 illustrates a graphical user interface (GUI) of an acceleration calculator for an athlete in accordance with one embodiment;

DETAILED DESCRIPTION

Figure 1A:
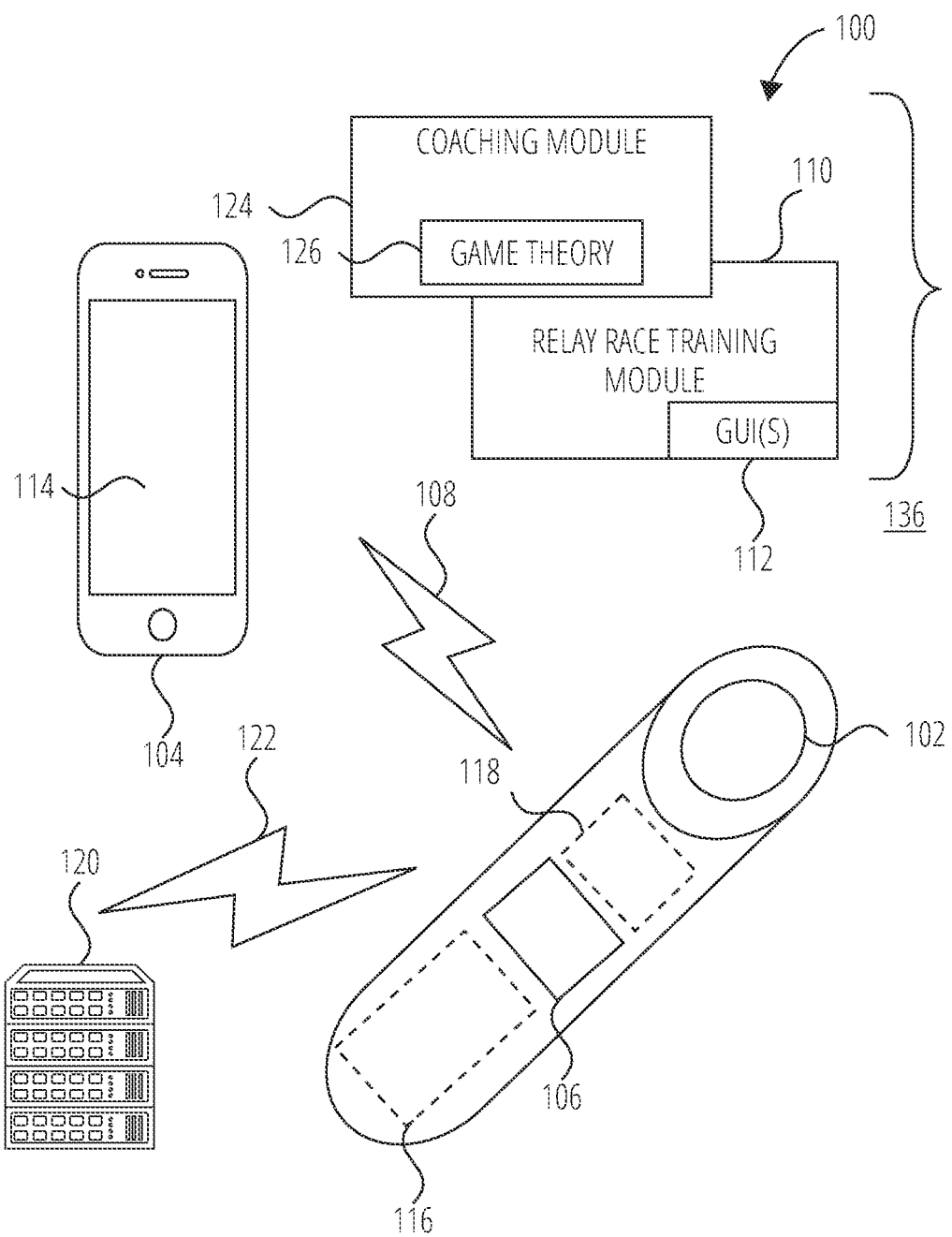
FIG. 1A illustrates a block diagram of a smart relay race training system in accordance with one embodiment.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Furthermore, unless otherwise clear from the context, a numerical value presented herein has an implied precision given by the least significant digit. Thus, a value 1.1 implies a value from 1.05 to 1.14. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Technology advancements with chip timing systems, motion sensors, accelerometer, inclinometers (e.g., measures the range of motion of upper extremities), etc., now allow for very precise measurements of timing, movements, and running methods.

Track and field differs from most other sports because it is solely measured in meters and seconds. A fraction of a second can make all the difference in track. Because of that, the technology that records data from track and field races and events must be relevant, precise, and accurate, as possible.

The smart relay race training system 100 may provide athletes with an interactive experience. The system 100 may include an electronic track baton device 102 that may include a display 106, mobile applications, analytics software, game theory algorithms, biometrics software, coaching software, eyewear/video recording software, etc.

Some of the embodiments herein detect, measure, and track a runner's swing including an optimal range of motion through the efficient recovery of the limb.

Some of embodiments detect and track a runner's body position which may be a central metric for improving performance including tracking arm movement so the athlete can adjust their arm movement to be the proper arm movement especially when carrying a baton device.

FIG. 1A illustrates a diagram of a smart relay race training system 100 in accordance with one embodiment. The system 100 includes an electronic track baton device 102 to be used in the field by an athlete. The system 100 may include a computing device 104, such as a mobile communication device, and applications 136. The computing device 104 may be a laptop, personal computer, notebook, tablet, iPad™, etc.

The applications 136 include software, hardware, firmware or a combination of software, hardware, and firmware. The applications 136 may include a relay race training module 110 which, when executed by a processor of the baton device 102 or the computing device 104, performs functions described herein.

The relay race training module 110 includes one or more graphical user interfaces (GUIs) 112, which are caused to be selectively displayed on a display 114 of the computing device 104. The GUIs 112 may selectively present captured relay race metrics of at least one athlete. The relay race training module 110 will be described in relation to FIG. 3A. The GUIs 112 will be described in relation to FIGS. 10-16. One or more of the GUIs 112 may cause to be displayed on a display device 106 of the baton device 102.

Figure 4:
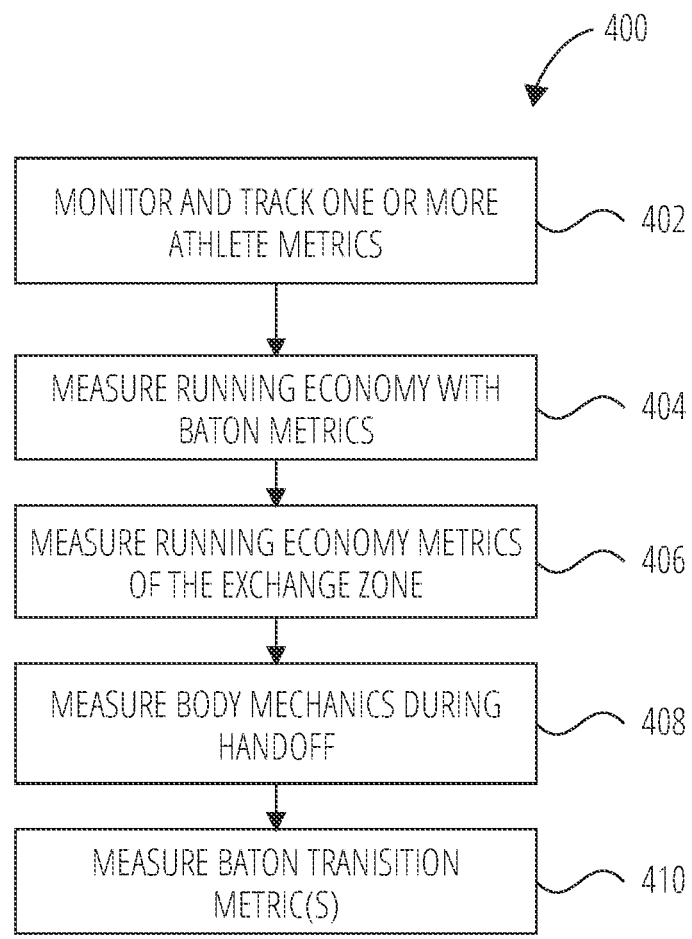
FIG. 4 illustrates a flowchart of a method for detecting baton transition metric(s) in accordance with one embodiment.
Figure 5:
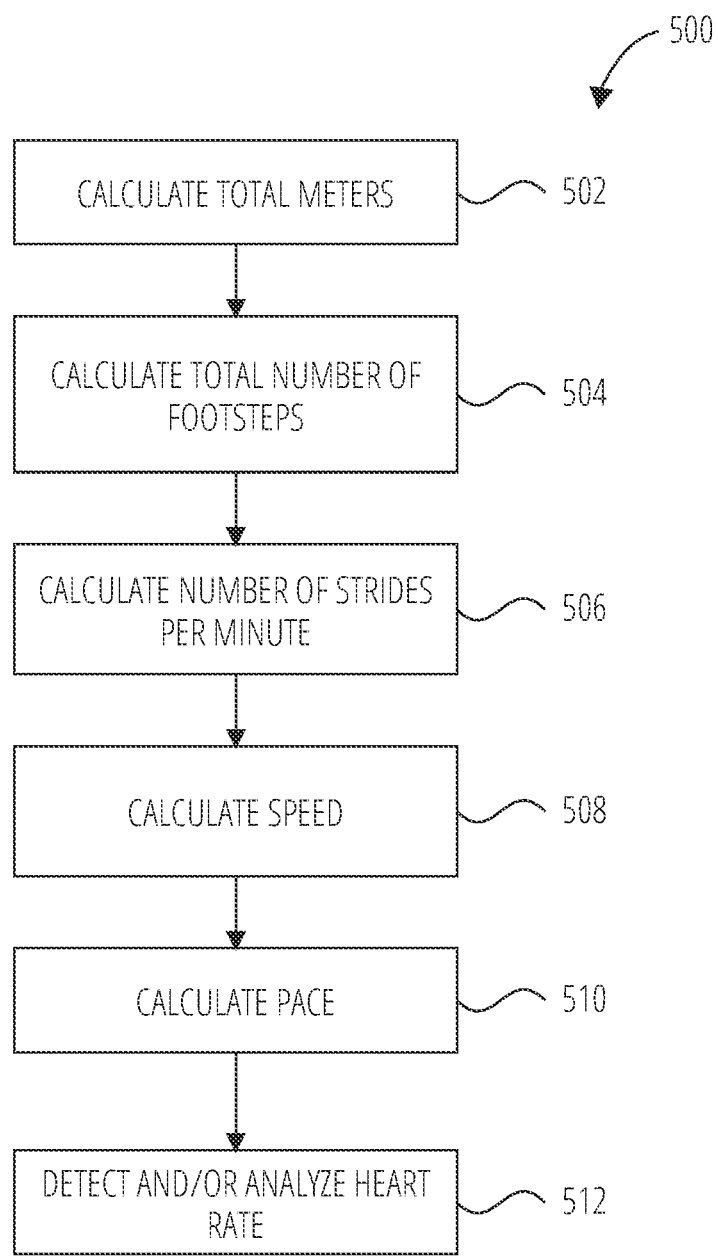
FIG. 5 illustrates a flowchart of a method for generating runner performance metric data in accordance with one embodiment.
Figure 6:
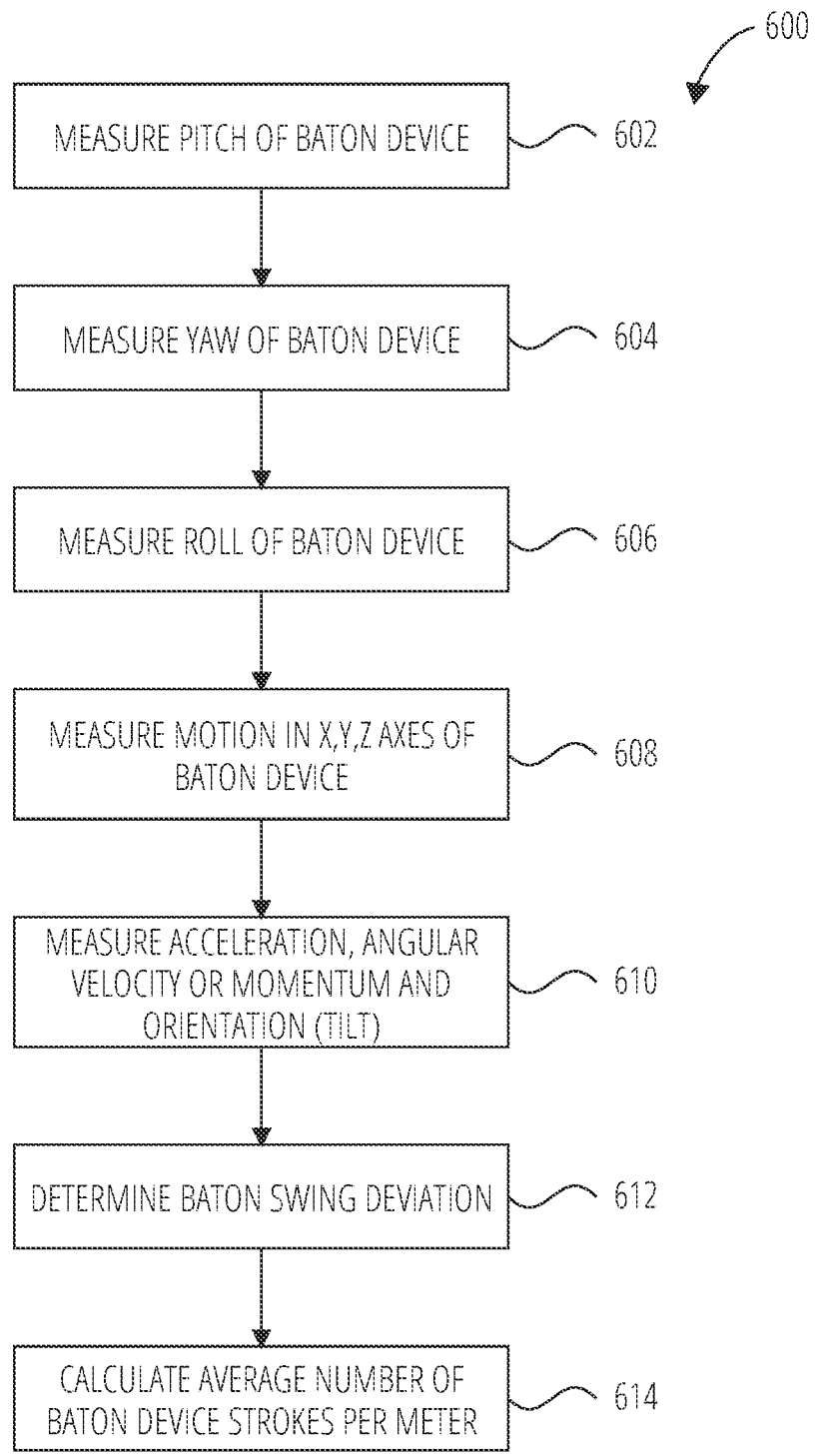
FIG. 6 illustrates a flowchart of a method for determining baton race metrics of the relay race phase coordinator in accordance with one embodiment.
Figure 7:
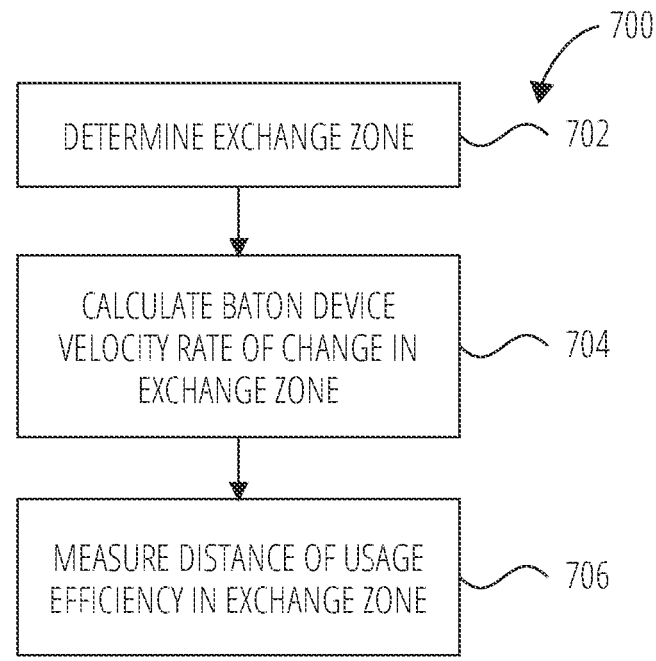
FIG. 7 illustrates a flowchart of a method for determining the running economy metrics associated with the Approach phase in accordance with one embodiment.
Figure 8A:
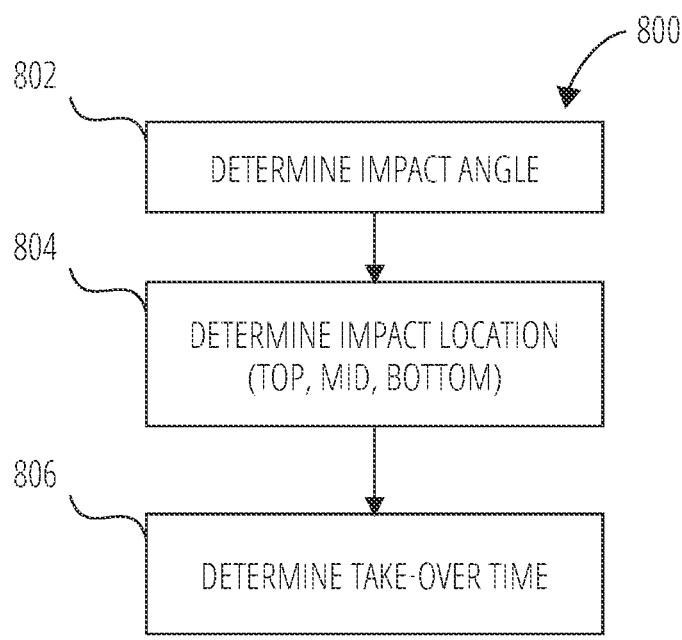
FIGS. 8A and 8B illustrate a flowchart of a method for proximity determination and the baton transition metrics associated with the Transition phase in accordance with one embodiment.
Figure 8B:
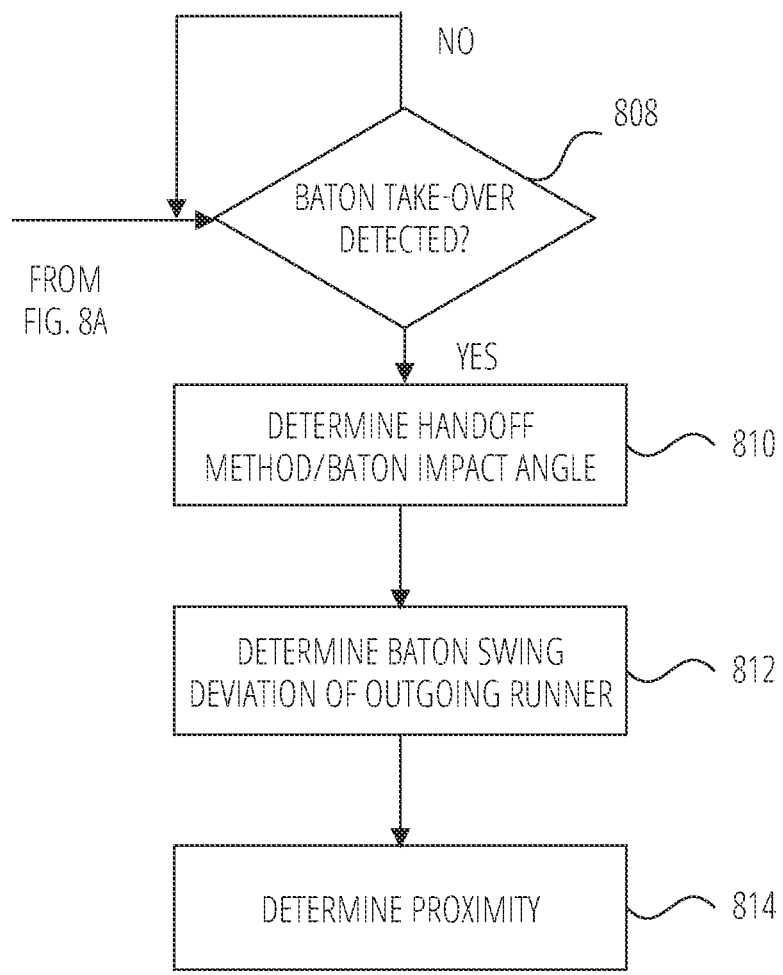
Figure 9:
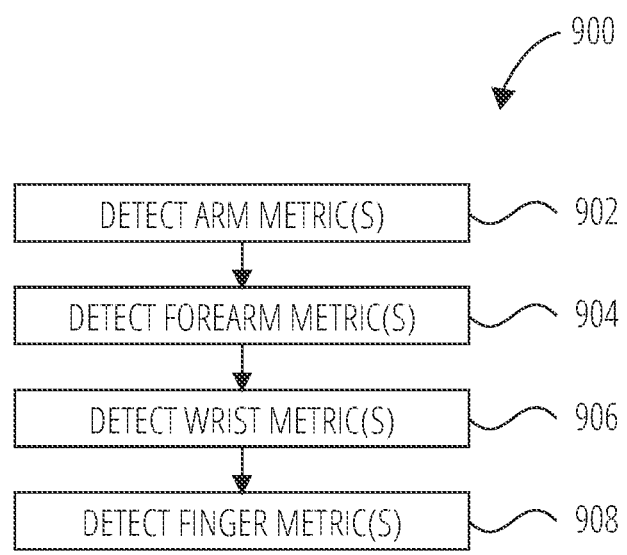
FIG. 9 illustrates a flowchart of a method for measuring the handoff body mechanics in accordance with one embodiment.

The applications 136 and the relay race training module 110 may include programming instructions stored on one or more non-tangible and non-transitory computer readable media, the programming instructions which, when executed, cause the processor to perform the method blocks of method 400 of FIG. 4, method 500 of FIG. 5, method 600 of FIG. 6, method 700 of FIG. 7, method 800 of FIGS. 8A and 8B, and method 900 of FIG. 9, and selectively display the GUIs discussed in more detail in relation to FIGS. 10-16. The GUIs also include programming instructions to cause the display of the metrics using icons and formats for side-by-side column and row presentation, for example of some metrics.

The electronic track baton device 102 tracks the performance metrics of each athlete in direct contact with the baton device 102 during a relay race. The electronic track baton device 102 will be described in more detail in relation to FIG. 2. The baton device 102 may be in wired or wireless communication with at least one computing device 104 via a communication link 108. The communication link 108 is shown as wireless. However, the communication media may use wired connectors and interfaces as will be described later. The baton device 102 includes one or more capacitive sensors 116 at a first end of the baton device 102 and one or more capacitive sensors 118 at a second end of the baton device 102. The second end is diametrically opposing the first end.

Projective Capacitive Technology (PCT)

The capacitive sensors 116 and 118 may use projective capacitive technology. In some embodiments, the baton's exchanges can be measured at +/−300 milliseconds (ms) or 0.3 seconds (equivalent to a human eye blink). But electrical relay switches can operate between 5 ms and 20 ms (a honeybee's wing flap) considering software rendering time, operating system, driver, and graphic card delays (i.e., "touch response budget time"). This feature is similar to Delta touch faucets that use capacitive sensitivity software controls where a faucet tap represents less than 300 ms or 0.3 sec, and a faucet grab represents more than 300 ms or 0.3 sec.

Analytics

The applications 136 and relay race training module 110 may use advanced analytics with sophisticated modeling techniques. By way of non-limiting example, JMP® Pro statistical discovery software from SAS® Institute is an example of modeling techniques and analytics that may be used with the system 100. JMP® Pro provides advanced analytics with various modeling techniques. The modeling techniques include predictive modeling with cross-validation using a number of different methods, modern modeling techniques, model comparison and averaging features, advanced multivariate techniques, reliability block diagrams, covering arrays, mixed models, uplift models, and advanced computational statistics methods.

The applications 136 applies activity modeling and prediction techniques specifically using: a) signal processing; b) machine learning; and c) statistics. The model is designed to: 1) collect data; 2) process/examine data; and 3) achieve predictive performance in simulation and in the field. The data is collected from the electronic track baton device 102.

The applications 136 of the system 100 determines 17 metrics represented as aggregated time-encoded data where JMP® Pro descriptive and predictive algorithms, or the like, look at the relationships among all of the variables to derive a more accurate view at every phase of a relay race.

In some embodiments, the system 100 may communicate via link 122 with a cloud computing system 120 or web-server system configured to execute web-server application, or cloud computing applications. At least one of the baton device 102 or computing device 104 may communicate with the cloud computing system 120 using wireless communications. Web-based reporting and data analytics may be performed at a cloud computing system 120. The cloud computing system 120 may execute instructions associated with game theory algorithms 126, such as "Nash Equilibrium" and "Non-Zero Sum." The cloud computing system 120 may execute instructions associated with three-dimensional (3D) animation, training tips, tutorials, technique video, COACHTUBE, COACH'S EYE (by TechSmith™ Corporation), and DARTFISH (by DARTFISH SA), for example. COACHTUBE provides online courses where a person can learn how to coach via instructional coaching videos. COACH'S EYE is a software system that allows users to capture video of a performance and slow-motion playback and analysis. DARTFISH provides video analysis of different sports performance.

Coaching Module

In some embodiments, the applications 136 may include a coaching module 124 that captures performance data and identifies running mechanics efficiently by combining sensors, software, and mobile applications. The coaching module 124 provides detailed analysis complete with specific training tips and drills enhanced with video analysis and tutorials. Runners are now able to know exactly how and why the techniques they implement are improving their performance and what they can do to take their training a step further. The details of the coaching module 124 will be described in more detail in relation to FIG. 3B. In some embodiments, the coaching module 124 may selectively provide information such as benefits as shown in the tables provided herein to the user, such as by selecting a displayed metric or related icon.

Game Theory

In track and field, it is important to identify the correct runner for each relay leg. Coaches can employ mathematical optimization methods using "Game Theory" algorithms 126 via computer software and/or a smartphone application platforms that can be run on computing device 104, the baton device 102 and/or cloud computing system 120. For example, a coach can apply the game theories of "Solution Concept," and/or "Pure Strategy." The Solution Concept is a formal rule for predicting how a game will be played. These predictions are called "solutions," and describe which strategies will be adopted by players and, therefore, the result of the game. The most commonly used solution concepts are equilibrium concepts, most famously "Nash Equilibrium." "Pure Strategy" refers to one of the options an athlete can choose in a setting where the outcome depends not only on one athlete's actions, but on the action of other athletes. This strategy will determine the action the athlete will take at any stage of the game.

The relay race training module 110 and coaching module 124 are shown separate from the baton device 102, the mobile device 104 and cloud computing system 120. This is because the applications 136 and modules 110 and 124, for example, may be used by and installed all or in part in memory of the baton device 102, the mobile device 104 and/or cloud computing system 120.

Interactive Eyewear Capabilities (Real-Time Athlete Performance Analysis)

Figure 1B:
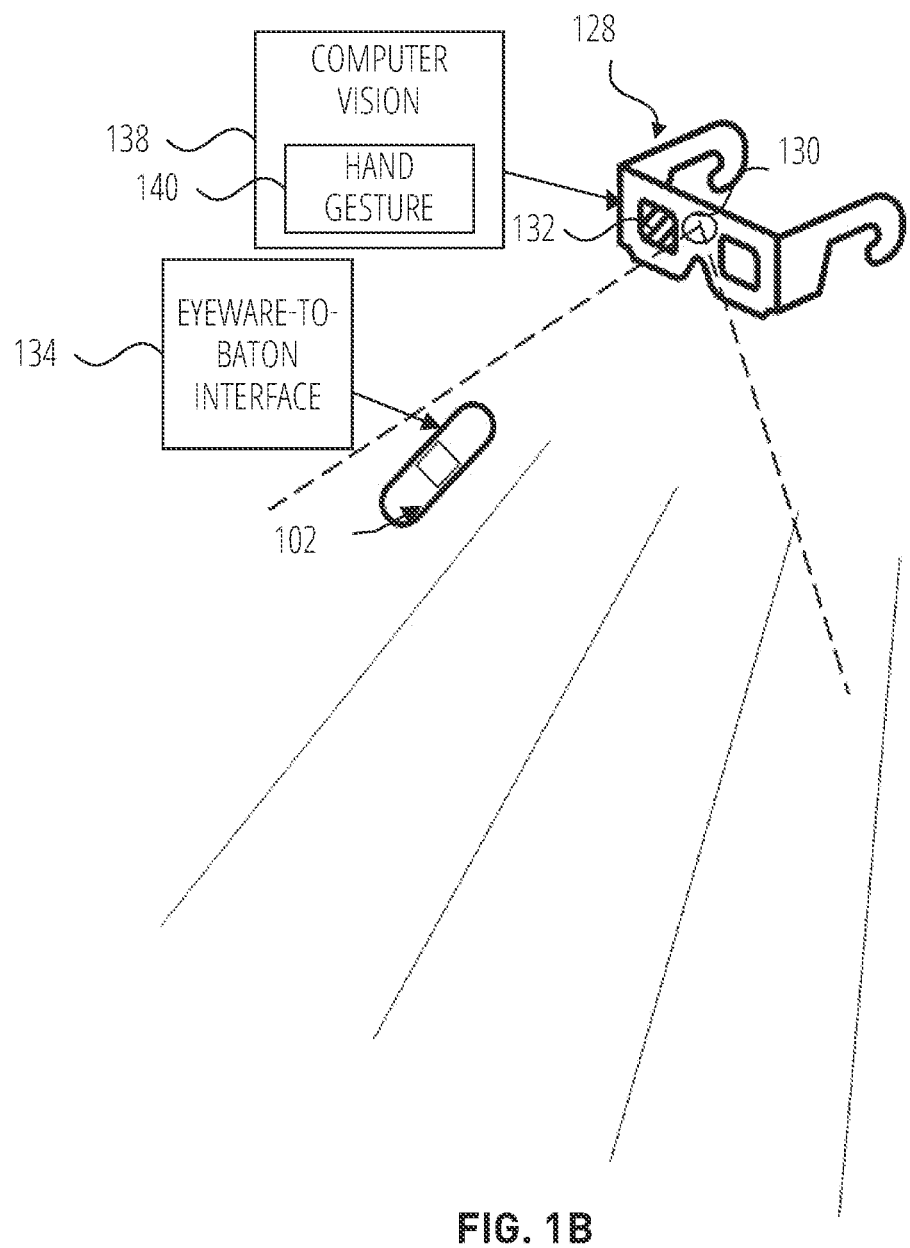
FIG. 1B illustrates a diagram of a smart relay race training system with eyeware device in accordance with one embodiment.

FIG. 1B illustrates a diagram of the smart relay race training system with eyeware device 128 in accordance with one embodiment. The eyeware device 128 may include eyeglass frames with see-through lenses 132. The eyeware device 128 may include a camera 130, such as a wide-angle camera denoted by the angled dashed lines. The applications 136 may also include an eyeware-to-baton interface module 134 and computer vision application 138. The computer vision application 138 may include a hand gesture module 140 to detect hand gestures of the user. In some embodiments, the eyeware device 128 may be used as the computing device 104 of FIG. 1B or used in addition to the computing device 104 in system 100.

The baton device 102 may be configured to interact with the eyeware device 128. Some interactive eyewear devices can communicate with a wireless communication link of the baton device 102 via BLUETOOTH™, for short-range wireless communications, to provide athletes an interactive experience. The eyeware device 128 may also communicate with the cloud computing system 120, computing device 104 and/or baton device 102. For example, the eyeware device 128 and the eyeware-to-baton interface module 134 will allow users to view training data aligned with the user's field of vision, such as by using computer vision applications 138. The baton device 102 can wirelessly acquire biomechanical data, and then transmit it to the eyeware device 128; thus, allowing athletes to view performance metrics in real-time (e.g., meters traveled with corresponding time, speed, heart rate intensity level, etc.). As shown, the baton device 102, especially when being handed off, will be in the field of view, denoted by the dashed lines, of the camera 130.

The baton device 102 utilizes the interactive eyewear's automatic wide-angle lens video recording of the race, which also supports and enables post activity analysis of video (e.g., ideal for video analysis of hand-to-hand baton exchanges). Some of the embodiments herein will detect and track a runner's arm action which accounts for about 40% of the running motion, create balance, control rhythm, and affect speed and endurance.

The computer vision applications 138 may capture the arms and hands of the runner wearing the eyeware device 128, as well as the arms, wrist, forearm, and fingers when in the field of view, of another runner especially during the approach phase 308, the handoff phase 310 and the transition phase 312.

The computer vision applications 138 may also be used to detect marks on the field or in the track area.

Figure 2:
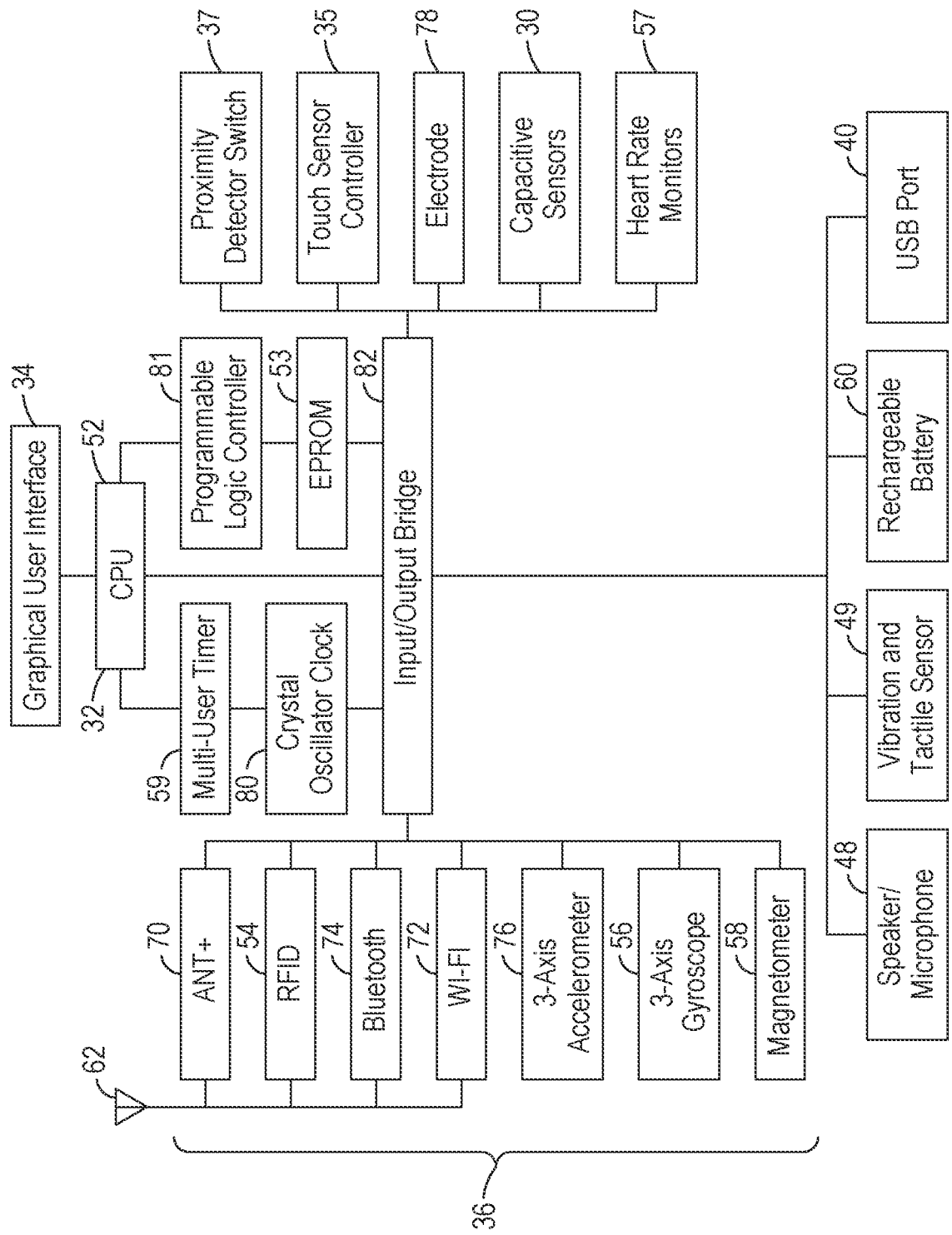
FIG. 2 illustrates a block diagram of a conventional electronic track baton device.

FIG. 2 illustrates a block diagram of a conventional electronic track baton device in accordance with one embodiment. The baton device 102 of FIGS. 1A and 1B may employ the system architecture as described in U.S. Pat. No. 9,126,094, titled "ELECTRONIC TRACK BATON DEVICE," which is incorporated by reference in its entirety. The system architecture includes central logic processing to process data, memory to hold data, and multiple interrelating electronic components, sensors and peripherals to communicate data. For example, the conventional electronic track baton device comprises a hollow cylindrical baton 15 having a first end spaced apart from a second end, and a constant circumference. The baton device may include a display device 34 disposed between the first end and the second end. A touch sensor is disposed within the display device 34. A plurality of externally sensitive capacitor sensors 30 (i.e., capacitive sensors 116 and 118) is provided. The capacitor sensors 30 comprise a biometric sensor switching 32. An existing metal in communication with the capacitor sensors 30 becomes an extension of the capacitive sensors 30. A proximity detector switch 37 is in operational communication with the capacitor sensors 30.

A plurality of interactive electronic components is disposed within the hollow cylindrical baton 15. The electronic components 50 are in operational communication and are in operational communication with the GUI 34 and the capacitor sensors 30. A power button 44 and a USB port 40 are disposed within the second end 22. The remaining electronic components are disposed within an approximate center of the hollow cylindrical baton 15. The remaining electronic components comprise a plurality of FPC 36, a speaker/microphone 48, a vibration and tactile sensor 49, an EPROM 53 disposed within the CPU 52, a radio frequency identification (RFID) 54, a transceiver 62, a 3-axis gyroscope 56, a heart rate monitor 57, a magnetometer 58, a multi-user timer 59, a rechargeable battery 60, a speedometer 64, a pedometer 66, a stride measure 68, an ANT+ wireless sensor network protocol 70, a WIFI™ 72 or wireless fidelity using short range communications, BLUETOOTH™ 74 or a short-range radio frequency communication protocol, a biometric sensor switching 32, a 3-axis accelerometer 76, an electrode 78, a crystal oscillator clock 80, a programmable logic controller 81, and an input/output bridge 82.

The advanced and adaptive network technology (ANT+) may be used for ANDROID™ type devices.

The baton device may include a pedometer, speedometer, and stride measure features to accurately measure steps taken and meters/distance traveled to achieve optimal electronic track baton device exchanges in relays, and to determine the most effective/efficient usage of an existing 30-meter baton exchange zone.

The baton device is configured to interact with various existing media via the BLUETOOTH™ 74, the WIFI™ 72, the transceiver 62, and the USB port 40. The baton device 102 is configured to provide split timing for a plurality of users via the multi-user timer 59.

The clock 80 interfaces with the multi-user timer 59, such as a stopwatch to provide a very precise frequency (32.678 kHz) for precise timing within 1/1000th of a second. The ANT+70 technology measures biometrics, distance, stride, steps, etc. The RFID 54 links each individual baton device 102 to a specific device, the team(s), athletes, coaches, etc.

The motion sensor components include a magnetometer 58, a 3-axis accelerometer 76, and a 3-axis gyroscope 56. The 3-axis accelerometer 76 configured to sense acceleration/g-forces. The gyroscope 56 senses the tilt/angular momentum used to detect movement and ultimately achieving 1:1 motion via "9 degrees of freedom." The accuracy ranges from approximately 0.01° to ±2°.

The capacitive sensors determine actual hand contact with the baton's surface by measuring the change in an electromagnetic field. Typical touch response time is 6 milliseconds with accuracy of >99%. The baton device 102 provides speaker functionality via the speaker/microphone 48 (FIG. 2), sensory feedback by replicating and simulating select coaching instructions, and verbal commands to athletes.

An inclinometer is a specific type of tilt/angle measuring technology that has similar functionality of a 3-axis gyroscope. The inclinometer may be placed within the housing of the baton device 102 and not attached to athletes. Specifically, the inclinometer/gyroscope technology senses the tilt/angular momentum used to detect movement. The inclinometer within the baton device 102 may include a 2-axis digital inclinometer, a Micro Electronic Mechanical Systems (MEMS) inclinometer, and a combination inclinometer with gyroscope.

In some embodiments, the baton device 102 of FIGS. 1A and 1B may include an e-inclinometer functionality, where the inclinometer is replicated via using an algorithm in software using as data the readings from the gyroscope 56, the accelerometer 76, and the magnetometer 58. The e-inclinometer simulates an inclinometer and produces essentially the same measurements of an inclinometer for the purpose of measuring the range of motion of upper extremities.

Applications

Figure 3A:
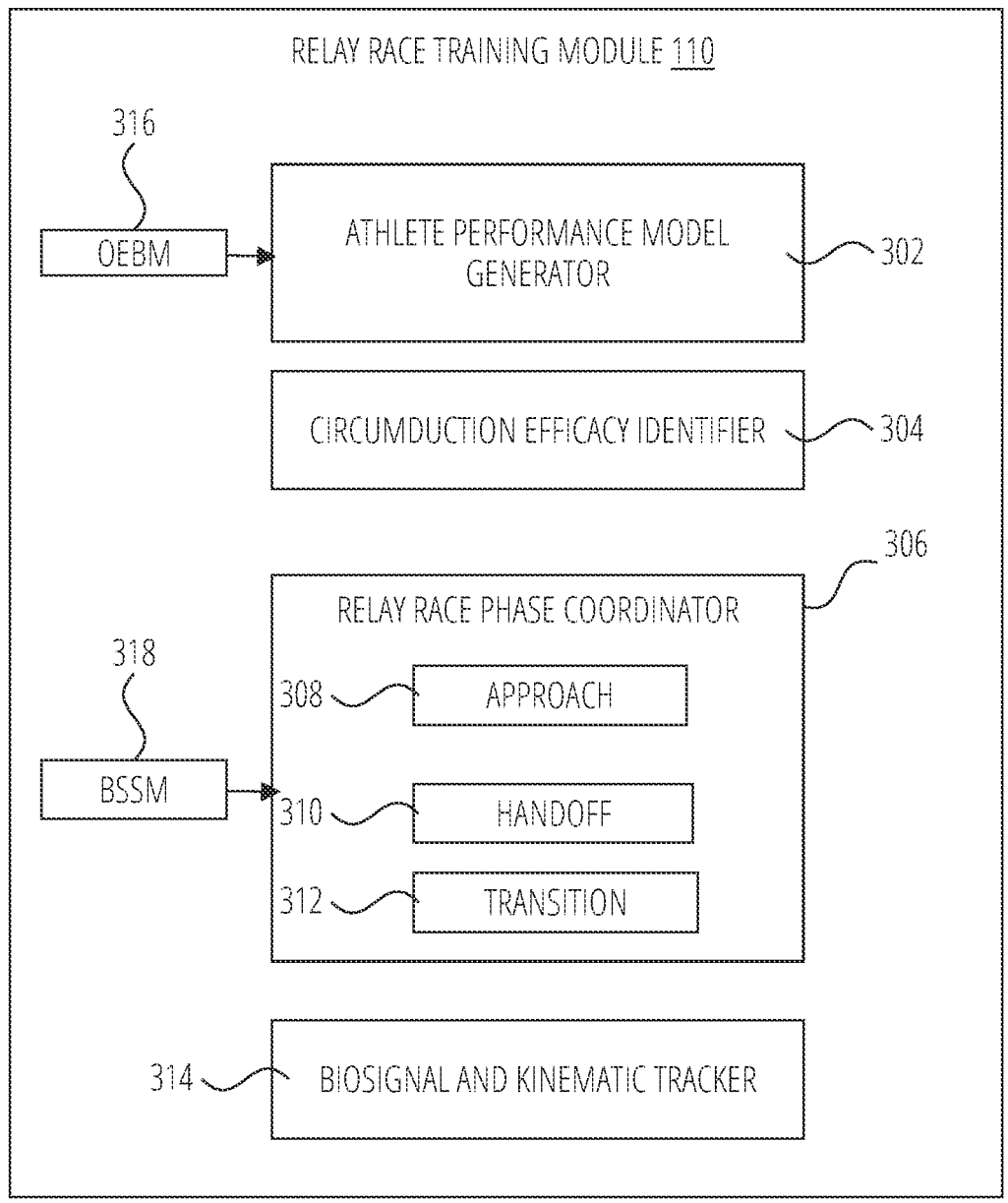
FIG. 3A illustrates a block diagram of the relay race training module in accordance with one embodiment.

FIG. 3A illustrates a block diagram of the relay race training module 110 in accordance with one embodiment. The relay race training module 110 may receive data generated by the baton device 102, which is processed and analyzed to provide a coach or athlete relay race data displayed in one or more GUIs 112. Example GUIs are shown in FIGS. 10-16. The relay race training module 110 may include an athlete performance model generator 302. The relay race training module 110 may include a circumduction efficacy identifier 304 which includes an athlete's activity model. The relay race training module 110 may include a relay race phase coordinator 306 to identify metrics during the approach phase 308, the handoff phase 310 and transition phase 312. One or more metrics are aligned with the three phases of a baton relay race (i.e., Approach, Handoff, and Transition) for the purpose of achieving better coaching and improved training and sporting performance.

Many athletes run different with a baton device 102. Few see in real-time the micro-level motions during relay baton exchanges; and even fewer understand or have a toolbox for remedying mistakes and errors. Each phase (i.e., Approach, Handoff, and Transition) of a relay race features a unique set of biomechanical principles and circumstances that may be tracked for performance improvements.

The relay race phase coordinator 306 may determine the posture/running style with the baton device 102. The posture/running style measure one or more of: 1) the angle between the forearm and the elbow; and 2) the stroke rate. For training purposes, the goal may be for #1, a forearm/elbow angle of 90°; and for #2 an optimal baton stroke rate.

Optoelectronic Biometric Module (OEBM)

To achieve optimal performance via heart rate training, the OEBM 316 translates heart rate signals that may be used by the athlete performance model generator 302. Athletes get the most effective workout by training at the right intensity level via the baton's embedded heart rate monitor sensors (e.g., Intensity=% of HRmax, Maximum 90-100%, Hard 80-90%, etc.). The OEBM 316 may provide the performance model generator 302 with data that highlights successful athlete's statistics for upcoming athlete's benchmarking purposes, for example. This is in line with the allowable International Association of Athletics Federations/IAAF guidelines (Rule 144.4(d) Personal Electronic Equipment): "Devices carried personally by athletes during a race such as heart rate or speed distance monitors or stride sensors, provided that such device cannot be used to communicate with any other person."

Biometric Surface Sensor Module (BSSM)

The baton device 102 introduces a forward-thinking automated track baton "Biometric Sensor-Switching Concept" for capturing runners relay split times via "Projective Capacitive Technology (PCT)." The relay race training module 110 includes a biometric surface sensor module (BSSM) 318. The BSSM 318 interfaces with the sensors and electrodes (not shown) to function as a touch switch that works by using the body's 22 pico-farads capacitance (static charge) in which an object must be touched to operate. The BSSM 318 may interface with the relay race phase coordinator 306 such as to determine one or more metrics associated with the handoff phase 310, for example.

Flexible printed circuits (FPC) are ergonomically embedded in the baton device 102 and identify alternating hand contact with sensors for calculating separate split times. Basically, the sensors (i.e., capacitive sensors 116 and 118) detect any change in the baton's baseline level of capacitance upon each hand contact. If a touch sensor (i.e., capacitive sensors 116 and 118) is connected to anything conductive (i.e., wire, metal bar, etc.), that conductive element becomes an extension of the touch sensor (i.e., ideal for baton exchange functionality).

Timing Accuracy

Split timing is >99% accurate within 1/1000th of a second (e.g., 49.568). Note that the fourth runner's split time and relay race total time precision is determined based on the total distance traveled in meters, which is automatically tracked by the baton when programmed for a certain relay race. For example, the 4×100 meter relay covers a total distance of 400 meters, the 4×400 meter relay covers 1,600 meters, and the 4×800 meter relay covers 3,200 meters among all four relay team runners. The final split time and relay race total time is captured/time-stamped using computer algorithms upon the fourth runner reaching the specified relay total distance traveled in meters, in relation to the start time of the first runner in a relay race. Precision also could be enhanced, crosschecked, and used in conjunction with existing timing system apparatus such as finish line timing computers, cameras, and/or RFID receiver configurations (e.g., ISOLYNX).

Motion Sensor Components (9 Degrees of Freedom)

The inclinometer functionality can be replicated via using an algorithm, the gyroscope, the accelerometer, and the magnetometer for accurate angle results. Specifically, the inclinometer/gyroscope technology senses the tilt/angular momentum used to detect movement. But the pitch of the baton is critical in relation to the baton hand contact location, and the magnetometer which is used to determine the direction of the magnetic field at a point in space in relation to the ground. The magnetometer also changes to the magnetic field around the baton to identify different gestures made.

Baton Top End Determination

This is measured by the hand touch point location on the baton using the capacitive sensors. For example, if the opposite end of the baton registers more untouched sensors, then this represents that the opposite end of the baton is the top end in order to complete the posture analysis.

Athlete's Ability to Hold a 90° Angle at the Forearm/Elbow

Baton swing is the measurement of degrees of the pitch and angle of the baton cylinder between the baseline address and the top of the baton swing. It is measured by the change in angle at address to the angle at the top of the swing. At baseline address, the baton is at zero degrees (0°), neutral, or horizontal to the ground. At the top of the swing, the baton is at 90° or parallel to the ground.

The optimal baton swing (i.e., one quarter swing of 360°) is a continuous motion where the baton cylinder is parallel to the ground (90°) or pointing skywards, and returning to zero degrees (0°), pointing forward. Most experienced runners average 90° during full running motion. Many amateur runners tend to over or under exaggerate the arm swing resulting in less-than-optimal running posture which can lead to potential injuries.

The raw data analysis may be focused and organized by technical mechanics at every phase by using the six degrees of freedom (DOF) raw data (pitch, yaw, and roll). The system 100 may analyze a multitude of desired metrics, either separately or by a concentrated area.

The relay race phase coordinator 306 may determine the inferential fatigue/endurance impact. The inferential fatigue/endurance impact may have a goal defined by a positive velocity rate change. The relay race phase coordinator 306 may determine how the body is reacting to activity intensity. The activity intensity may have a goal of maximum effort heart rate zone. The relay race phase coordinator 306 may provide precise data to employ strategies to adjust the turnover/stride rate. For training purposes, the goal of the turnover/stride rate may be 170 to 190 steps per minute. The relay race phase coordinator 306 provides distance, speed, and time. The goal is to reach a top-end speed point in the exchange zone.

The relay race phase coordinator 306 may determine the proximity of the incoming runner and/or outgoing runner. The proximity may have a goal of double arm's length.

The proximity determination is a combination of the baton impact and transition phases using the software/algorithms. Important here is analyzing the baton angle at transition impact, and the subsequent arm swing motions via the baton. The method for determining proximity will be described in more detail in FIG. 8B.

The relay race phase coordinator 306 may determine a good hand target. The goal is to provide a finger to thumb spread of 6 to 10 inches. The relay race phase coordinator 306 may measure the distance usage efficiency within a 20-meter to 30-meter exchange zone. For training purposes, the usage efficiency may have a goal of at least 50%. The usage efficiency is described in more detail in relation to FIG. 7. For example, metrics captured by the relay race phase coordinator 306 may include six general runner metrics, as will be described in relation to FIG. 5, and 11 specific relay baton exchange metrics, as described in relation to FIG. 6.

The relay race training module 110 may include a biosignal and kinematic metrics tracker 314, which identifies the metric, metric functionality, and metric benefit(s). Table 1 shows a list of metrics, metric functionality, and metric benefits. The GUIs may provide an explanation associated with the functionality and benefits.

The 11-core baton exchange/three phases which could be color-coded include: 1) Approach phase (Green and three metrics); 2) Handoff (Tan and four metrics); Transition (Blue and three metrics). The demarcation of phases are the inventor's novel interpretation of the phases during training or competition related to relay races.

However, any metric can be used in any combination for analysis purposes using the software/App and GUI presentation. For example, Athlete Comparison (FIG. 16) shows nine metrics; The Approach (FIG. 10) shows eight metrics; etc. But the 11 core baton exchange metrics, broken down in three phases as identified above, must always be presented separately before any presentation adjustments.

TABLE 1

| Metric | Functionality | Benefit |
| --- | --- | --- |
| Distance (meters) | Calculates the total meters for running events. | Provides the ability to analyze technical mechanics at any distance and/or running phase (i.e., Drive, Maximum Velocity, and Maintenance). Critical element used in the "Exchange Zone Usage Efficiency" metric. |

TABLE 1-continued

| Metric | Functionality | Benefit |
|---|---|---|
| Footsteps (no. of footsteps) | Calculates the number of footsteps. | Provides precise footstep data used to calculate stride length. Stride length is the distance between footsteps of the same foot, and is used in determining stride rate. |
| Stride Rate (strides/min) | Calculates the number of strides per minute (runner turnover). The optimal stride rate is between 170 and 190 steps per minute (i.e., 85-95 steps per minute each foot). | Provides precise data to employ strategies to adjust the turnover/stride rate (SR) in relation to gaining or decreasing speed at select running phases (i.e., higher and lower SR, respectively). Ideal when analyzing exchange zone and curve running. |
| Speed (meters/second) | Calculates the speed in relation to distance covered per second. | Provides precise speed data for accurate placement of the "Go" Mark tape for outgoing runners in exchange zones. Critical element used in the "Exchange Zone Velocity Rate" metric. |
| Pace (seconds/ meter) | Calculates the pace as seconds per meter in relation to time and distance covered. Derived pace time is compared to target pace time. Example: Target Pace (400 m Split Time) 47 sec = 0.1175 sec/meter 48 sec = 0.1200 sec/meter 49 sec = 0.1225 sec/meter 50 sec = 0.1250 sec/meter | Provides real-time tempo to determine if each individual runner (R) is on pace to achieve a certain split time, or relay team total projected time. Where total projected time (TPT) is: (R1 + R2 + R3 + R4) − 2 seconds = TPT |
| Heart Rate (beats/ minute) | Detects the change in heartbeats through pulse/blood flow using optical sensing. | Determines how the body is reacting to activity intensity. The composure or poise factor. |

Table 2 provides a list of running economy metrics for the Approach phase 308. Running economy represents the foundational concept that is correlational to any phase of running, thus is important to ensuring optimal baton mechanics.

phase, these metrics also apply to all phases. For example, the Approach phase determines metrics that should be correlated to the progression of running a relay race. The

TABLE 2

| Metric | Functionality | Benefit |
|---|---|---|
| Running Economy: Baton Swing Deviation (degrees) | Measures pitch, yaw, and roll (9 Degrees of Freedom) during general running and at the baton/hand impact point. +/− from baseline 0°. | Determines the inferential drag (air resistance) effect on the baton device. |
| Running Economy: Baton Stroke Rate (strokes/meter) | Calculates the average number of baton strokes per meter at each baton transition interval. | Determines the posture/running style with baton device and the impact on split time. |

Table 3 provides a list of running economy metrics associated with the Approach phase 308. While Table 2 and Table 3 metrics are described to be within the Approach Approach phase specifically shows the useful mechanics required just before actually interacting with other athletes on the same relay team.

TABLE 3

| Metric | Functionality | Benefit |
|---|---|---|
| Exchange Zone: Velocity Rate (meters/second) | Calculates the baton's velocity rate of change within the exchange zone (acceleration/deceleration). Incoming Runner - within the 20-meter to 30-meter exchange zone before and during baton transition. Outgoing Runner - within the 20-meter to 30-meter exchange zone upon baton take-over. | Provides the intensity level at different running phases (i.e., Drive, Maximum Velocity, and Maintenance). Determines the inferential fatigue and speed endurance impact (e.g., "hitting the wall" due to glycogen and/or lactic acid effects). |

TABLE 3-continued

| Metric | Functionality | Benefit |
| --- | --- | --- |
| Exchange Zone: Usage Efficiency (percent) | Measures the distance usage within the 20-meter to 30-meter exchange zone as a function of total meters at each baton transition interval. Where efficiency is: (Baton Total Meters (BTM) − Zone Meters Start (ZMS)/Zone Total Meters (ZTM) = Zone Efficiency (ZE). For example, for first two zones of a 4 × 100: Zone 1 (103 m − 80 m/30 m = 76% ZE); Zone 2 (207 m − 180 m/30 m = 90% ZE). | Determines top-end speed point. Provides distance strategy for each relay leg. Parameters are adjusted for each type of relay race - 4 × 100, 4 × 200, 4 × 400, 4 × 800, Sprint/Distance Medleys, etc. |

Table 4 is body mechanics during the Handoff phase 310.

TABLE 4

| Metric | Functionality | Benefit |
| --- | --- | --- |
| Arm: Angle Extension (degrees) | Extension (Straightening). Obtuse Angel 91° thru 180°. Reflex Angel 181° thru 269°. | Determines the proximity distance of the incoming and outgoing runner. |
| Forearm: Rotation (degrees) | Pronation (Inward), Supination (Outward). +/− from baseline 0°. | Determines the extent of the outgoing runner receiving the baton device in a natural position. |
| Wrist: Angle Flexion (degrees) | Palmar flexion (Palm Up). Dorsiflexion (Palm Down). +/− from baseline 0°. | Determines the extent of the outgoing runner receiving the baton in a natural position. |
| Fingers: Abduction/ Adduction (no. of node touchpoints) | Spreading or closing of fingers. Calculates the no. of simultaneous touch points via mutual capacitance technology. | Determines if the outgoing runner provides a good hand target for incoming runner. |

Table 5 is the baton transition metrics during the Transition phase 312.

TABLE 5

| Metric | Functionality | Benefit |
| --- | --- | --- |
| Baton Transition: Impact Angle (degrees) | Vertical - Right Angle 90°. Horizontal - Straight Angle 180°. Upward - Acute Angle less than 90°. Downward - Reflex Angle 270° thru 360°. | Determines the method for which the baton is passed: 1) Push-in 2) Downsweep/Overhand Pass 3) Upsweep |
| Baton Transition: Impact Location (top, mid, bottom) | Elevation (High). Depression (Low). Identifies the touch point location via mutual capacitance technology. | Determines the need to rearrange the baton device before the next handoff. |
| Baton Transition: Take-over Time (milliseconds) | Applied as the change in milliseconds upon simultaneous hand touch by both runners, and completed once solely in the hand of the outgoing runner. Calculates the decisive individual split time sas a function of total elapsed time. | Determines the extent of high-speed handoffs (1 sec = 1,000 ms). |
| | "Biometric Sensor-Switching" process via mutual capacitance technology. | |

The baton device 102 may provide biosignal and kinematic information to users in real-time directly on the built-in touchscreen, smartphone/mobile device app, other output devices such as stadium videoboard or scoreboard displays, live television broadcast or webcast data feeds, as well as through software and/or web-based reporting and analytics.

The relay race training module 110 may include one or more algorithms aggregating time-encoded data and applying multivariate statistical analysis and pattern recognition of variables (e.g., Cluster Analysis, Cross-Sectional Analysis, Variance Analysis, Linear Discriminant Analysis, and Recursive Partitioning). The algorithms may develop relationships among all of the variables to derive a more accurate view at every phase of a relay race. Multiple data sets are stored and tracked to provide coaches meaningful relationships by cross-referencing information and representing trends using the GUIs 112.

Intervention—Activity Modeling Via "Circumduction Efficacy"

The inventor developed a framework for enhancing performance via "Intelligent Athlete Performance." Core elements are: 1) Insight Through Discovery; 2) Monetizing the Value of Interventions; 3) Innovation to Improve Outcomes; 4) Benchmarking Achievements; and 5) Integration of Meaningful Relationships. It leverages new data streams and uses software to tell a story about athletes based on movement data from multiple device sensors. It accomplishes this by using activity modeling, incorporating biosignal and kinematic metrics, data aggregation, and algorithms.

Activity Modeling

The system 100 applies activity modeling and prediction techniques specifically using: a) signal processing; b) machine learning; and c) statistics. The model is designed to: 1) collect data; 2) process/examine data; and 3) achieve predictive performance in simulation and in the field ("Identify. Interpret. Improve."). There are 17 proprietary metrics aligned with the three phases of a baton relay race (i.e., Approach, Handoff, and Transition) for the purpose of achieving better coaching and improved training and sporting performance. The metrics are categorized by: a) 6 general metrics; and b) 11 specific relay baton exchange metrics. The system 100 provides biosignal and kinematic information to users in real-time directly on the built-in touchscreen, smart phone/mobile device app, as well as through software and/or web-based reporting and analytics. It accomplishes this by aggregating time-encoded data and applying multivariate statistical analysis and pattern recognition of variables. Descriptive and predictive algorithms look at the relationships among all of the variables to derive a more accurate view at every phase of a relay race (e.g., Cluster Analysis, Cross-Sectional Analysis, Linear Discriminant Analysis, Multivariate Analysis, Statistical Analysis, Pattern Recognition, Recursive Partitioning, and Variance Analysis). Rarely should data be analyzed in isolation; thus, multiple data sets provide athletes and coaches meaningful relationships by cross-referencing information and seeing trends.

The relay race training module 110 may develop athlete training improvement techniques by analyzing user requirements and use cases through a circumduction efficacy identifier 304. The circumduction in this context is the combination of different motions and body movements occurring simultaneously in several planes. The circumduction motions or movements may include abduction/adduction, elevation/depression, flexion/extension, palmar flexion/dorsiflexion, and pronation/supination.

The hand gesture module 140 may be used to detect circumduction motions or movements such as abduction/adduction, elevation/depression, flexion/extension, palmar flexion/dorsiflexion, and pronation/supination. The detected circumduction motions or movements may be played back to the user, athlete, or coach. The goals of the motions or movements may be overlaid on the captured video to see offset in actual circumduction motions or movements metrics and goal circumduction motions or movements.

The hand gesture module 140 may be used to detect certain hand gestures of a user to control the operation of the eyeware device 128.

Motion Sensor Components (9 Degrees of Freedom)

The inclinometer functionality can be replicated via using an algorithm, the gyroscope, the accelerometer, and the magnetometer for accurate motion/angle results. Specifically, the inclinometer/gyroscope technology senses the tilt/angular momentum used to detect movement. The pitch, yaw, and roll of the baton in relation to the baton hand contact location, and the magnetometer are used to determine the direction of the magnetic field at a point in space in relation to the ground. The magnetometer also changes to the magnetic field around the baton to identify different gestures made.

Anatomical Motions Using Relay Baton

The circumduction efficacy identifier uniquely ties together body motions/movements with relay running and baton exchange techniques. Motion in this context is described using specific anatomical terms. Circumduction can be abstracted purely into mathematical functions within units of a circle (0° to 360°) in the complex plane (e.g., hand traces a circle, and the arm traces a cone).

Central to the baton's software/algorithms motion determinations (i.e., 9 DOF) is the change at +/− from baseline 0° (also referred to as "neutral"). The baseline address varies based on the anatomical position/description. But, for the most part, the baseline represents the midline of the body/hand, or the center of the body/hand for tracking baton motions while running. This aligns with the 17 color-coded metrics.

Software/Algorithms Translation (17 color-coded metrics) includes Abduction and Adduction, Elevation and Depression, Flexion and Extension, Palmar flexion and Dorsiflexion, and Pronation and Supination. Abduction and Adduction includes: 1) Fingers—spreading the digits apart away or toward the hand centerline; and/or 2) any motion away or towards the midline of the body. Elevation and Depression may include movement above and below the horizontal center of the body. Flexion and Extension may include movement that decreases or increases the angle between body parts. Palmar flexion and Dorsiflexion may include movement of the flexion (palmar flexion or palm up) or extension (dorsiflexion or palm down) of the hand at the wrist. Pronation may include Pronation at the forearm, which is a rotational movement where the hand and upper arm are turned so the thumbs point towards the body. Supination may include Supination of the forearm, which occurs when the forearm or palm are rotated outwards. For example, the swinging action made during the track and field relay baton exchange is a prime example of circumduction. Efficacy for this purpose represents analyzing circumduction, and applying interventions to produce a desired effect in track and field. Most notably, get the baton to the finish line first by producing the quickest handoffs without dropping the baton. Coaches should pursue improvements based on the value of interventions through quantified experimentation, not tradition only. Analyzing circumduction means reviewing the six general metrics, along with the 11-relay baton exchange sport-specific metrics identified herein.

Running Economy

The system 100 presents data on different running patterns for all levels of athletes. The system 100 provides data in terms of posture, risks of injury, and engagement of energy systems (e.g., technique for running 400 meters requires that athletes distribute speed and energies in the most efficient manner over the total racing distance).

Posture (Baton Swing Deviation and Baton Stroke Rate Metrics)

Energy efficiency of arm swing and its potential in adjusting the momentum of the body have been utilized in sports. Sprinters make use of the contribution of arm swing on the linear momentum in order to get a higher forward acceleration.

Kinematics of human running involves specific coordination patterns between upper and lower body segments which are dependent on walking/running speed. At walking/running speeds higher than 0.8 meters per second (m/s), arm swing increases, the arms move out-of-phase, while the frequency of movement is synchronized with stride frequency, coinciding with a 1:1 frequency locking between arm and leg movements. Stride frequency is the number of steps taken in a given amount of time or over a given distance. This is sometimes referred to as cadence. For example, short quick strides (common with sprinters through 400 meters) increases stride frequency but reduces stride length (M. P. Ford, R. C. Wagenaar, K. M. Newell (2007). Arm constraint and walking in healthy adults. Gait & Posture, 26, 135-141.). Risk of Injury (Footsteps, Stride Rate, Baton Swing Deviation, and Baton Stroke Rate Metrics)

Flawed high-speed running techniques can lead to over exaggerated arm swing, over striding, and injury. Improved speed and performance should be achieved with good running technique. Optimally, foot strike takes place beneath the center of mass, with the support leg perpendicular to the ground. However, some considerations in improving speed is to increase stride length and stride frequency, which could cause over striding. Over striding is directly linked to injuries by taking longer strides to increase speed. When athletes land the foot way out in front of the body (center of mass), it can in effect act as a brake with every step and jam the leg for a locked knee and heel. This places great stress on the bottom of the foot (arches, plantar fascia), soleus and calf, back of knee (popliteal tendon) and upper hamstring leading to both acute and overuse injuries such as tendonitis (Thomas, Latif. (2022). Stride Length and Stride Frequency: An Indirect Approach. West of Scotland Sprint Training & Coaching Information).

Engagement of Energy Systems at 400 Meters (Distance, Speed, Pace, Baton Swing Deviation, and Baton Stroke Rate Metrics)

The 400 meters is an oxygen-deficient event. This means that the level of oxygen absorption is below that which is necessary to supply the ATP (adenosine triphosphate) requirement. The energy used during the 400-meter run is derived from the breakdown of high energy phosphate compounds and from the splitting of glycogen to lactic acid. This event primarily focuses on two anaerobic systems, the ATP-PC (Alactic Phosphocreatine) and lactic acid systems.

Speed endurance is a combination of two major bio-motor abilities: speed and endurance. Speed is the ability to apply high speed of movement to a body or body part (see posture above). Endurance is the ability to apply force for long time periods (Distance, Speed, Pace Metrics).

Speed at 100 and 200 meters can be a tremendous advantage to the 400-meter runners, but only if they learn to distribute their energy systems properly. For example: 100 Meters—Should use acceleration to reach maximum controllable speed in 4-7 seconds as opposed to achieving maximum speed in 3-4 seconds; 200 Meters—Should take advantage of ATP stores by using maximal acceleration during first 40-60 m. Generally, the outstanding 400-meter runner will have approximately a one- to two-second differential between their best open 200 meters, and the time it takes them to run the first 200 meters of the 400-meter dash (Hart, Clyde. (2007). Baylor Sprint Relay Exchange and Speed Development. USATF Training Seminar).

Various example categories of runners include Beginner; Elite; Amateur; and Professional. A Beginner runner may be a Novice (0-3 years) and little to no experience in the sport or a particular event. An Elite runner may have +5 years of experience in the sport or event, and participated in high-level or championship competitions. An Amateur runner has experience in any competitive sport participation, but not on a pay-for-service basis. A Professional runner is on a pay-for-service basis.

Club Track and Field Athletes (Amateur/Beginner or Elite)

About 100,000 members participate with USA Track and Field (USATF). Fifty-seven (57) USATF Associations oversee the sport and its +2,500 clubs at the local level. Member organizations include the U.S. Olympic Committee, National Collegiate Athletic Association (NCAA), National Association of Intercollegiate Athletics (NAIA), Road Runners Club of America, Running USA, and the National Federation of State High School Associations. The Amateur Athletic Union (AAU) track and field membership and clubs represents half of USATF. Typically, ages range from 6-19.

High School Track and Field Athletes (Amateur/Beginner or Elite)

According to the National Federation of State High School Associations (NFHS), there are about 1.1 million high school students that participate in outdoor track and field sports. This estimate includes +600 thousand male and +500 thousand female students in more than 19,000 schools with track and field programs. Typically, ages range from 14-19. On the contrary, examples of professional track and field (T&F) athletes include T&F Olympian, T&F Olympic qualifier, and T&F Semi-Pro or Pro Runner under a Sports Label.

Figure 3B:
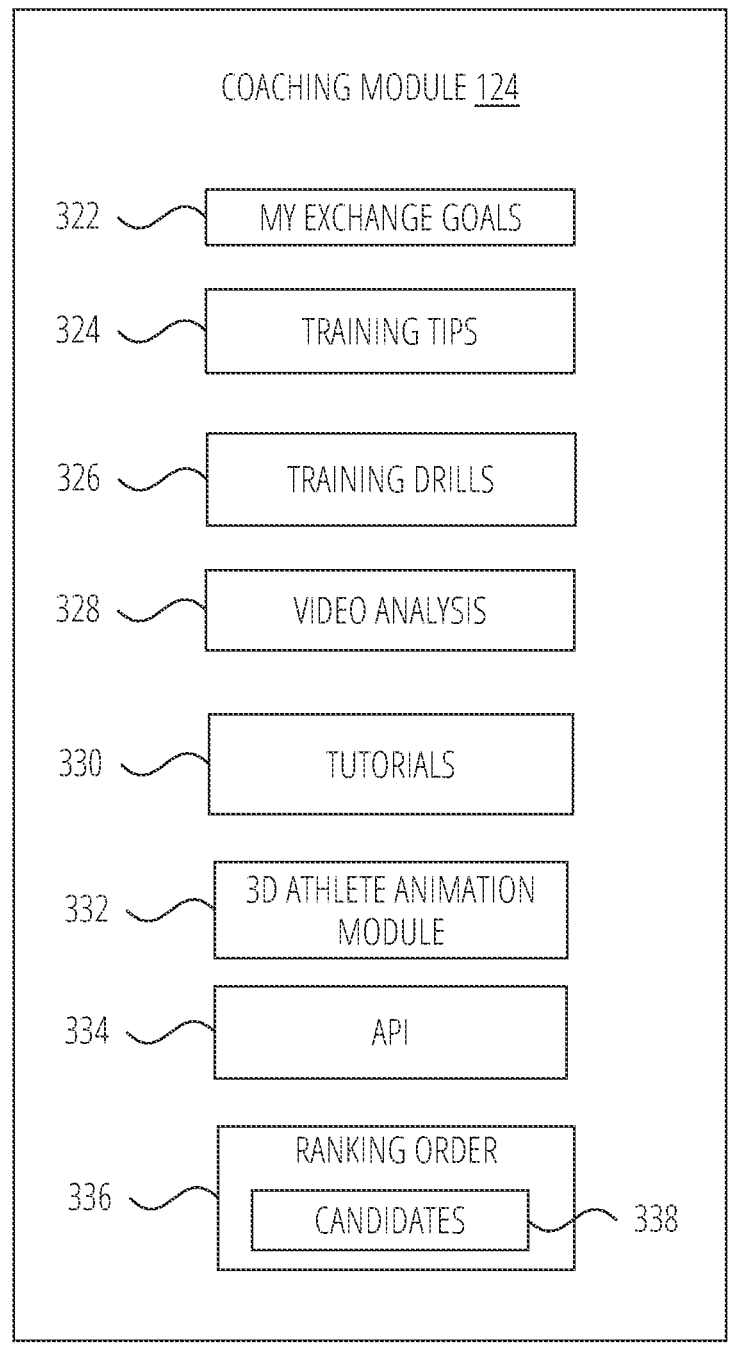
FIG. 3B illustrates a block diagram of the coaching module in accordance with one embodiment.

FIG. 3B illustrates a block diagram of the coaching module in accordance with one embodiment. Through the coaching module 124 and/or web-based reporting and analytics, the system 100 allows for coaches to provide sport-specific and directed/recommended training tips 324, training drills 326, video analysis 328, tutorials 330, and technique videos, etc., using data points acquired from the baton device 102. The coaching module 124 may include a three-dimensional (3D) athlete animation module 332 to create 3D Animation of athletes (i.e., Avatars). The coaching module 124 accomplishes this by aggregating time-encoded data and applying multivariate statistical analysis and pattern recognition of variables (e.g., Cross-Sectional Analysis, Variance Analysis, Cluster Analysis, Linear Discriminant Analysis, Multivariate Analysis, Pattern Recognition, Statistical Analysis, and Recursive Partitioning). The system 100 may be configured to find/search for relationships among the variables to derive a more accurate view at every phase of a relay race. Multiple data sets may provide coaches meaningful relationships by cross-referencing information and seeing trends. For example, ZEPP smart coach applications from ZEPP Labs Inc. may be used.

The functionality of the coaching module 124 may be compatible with other track and field online platforms such as COACHTUBE, COACH'S EYE (by TechSmith orporation), and DARTFISH (by DARTFISH SA), for example. The coaching module 124 may include an application programming interface (API) 334 for interfacing with known coaching applications.

The coaching module 124 can employ mathematical optimization methods using "Game Theory" algorithms 126 such as "Non-Zero-Sum Game" (i.e., we all win together or lose together) via computer software and/or a smartphone app (See "PlaySight™ Smart Court" Tactical 3D Game Management).

The baton device 102 is capable of producing sensory feedback by replicating and simulating select coaching instructions and verbal commands to athletes. In operation, the microprocessor, in communication with the memory, can be programmed to include vibration via a vibration unit (not shown) and audio prompts via the speaker/microphone 48 (FIG. 2) for predetermined workouts. For example, the coaching module 124 can create My Baton Exchange Goals 322 that allows the athlete to set goals to aim for a championship-quality relay race, for example. Using a Main Menu GUI setup and choosing from a list of preset goals, a user may customize their own goals, or choose to model their goals after the best baton metrics or relay races of another athlete, such as a professional athlete or an Olympian, for example.

In some embodiments, the applications 136 or the coaching module 124 may include a ranking order module 336 with a list of athlete candidates 338. The coaching module 124 may be used by both a coach and an athlete. The ranking order module 336 may be used by a coach training the athletes using baton device 102, such that the athlete's metrics are stored in the cloud computing system 120, in computing device 104 or the baton device 102. The ranking order module 336 may be used by an athlete so that they can determine their own ranking order, which may be displayed via a GUI.

FIGS. 4-7, 8A and 8B show flowcharts of methods performed by the system 100. The method steps may be performed in the order shown or a different order. One or more of the method steps may be performed contemporaneously. One or more of the steps may be omitted or other steps added. During the relay race, the baton device 102 includes motion sensors such as an accelerometer, gyroscope, and magnetometer to measure various metrics of the baton device 102.

FIG. 4 illustrates a flowchart of a method 400 for detecting baton transition metric(s) in accordance with one embodiment. In block 402, the method 400 may monitor and track one or more athlete metrics, as shown in Table 1. The metrics in Table 1 are related tracked for each individual athlete during the corresponding track distance for the athlete. During the transition phase of the baton device 102, the next athlete may also be detected using the capacitive sensors, the metrics for the next athlete of the team begins tracking. The baton device 102 stops tracking a previous athlete during the distance ran by the next athlete. For any relay race the performance of all athletes are tracked over the total of a relay race, as each athlete is changed.

In block 404, the method 400 may measure running economy with baton metrics. The metrics of the running economy are described above in relation to Table 2. In block 406, the method 400 may measure running economy metrics of the exchange zone. Table 3 above describes the exchange zone metrics of the Approach phase 308. In block 408, the method 400 may measure body mechanics during handoff. Table 4 describes the body mechanics during the Handoff phase 310.

In block 410, the method 400 may detect baton transition metric(s). Table 5 is the baton transition metrics during the Transition phase 312.

FIG. 5 illustrates a flowchart of a method 500 corresponding to block 402 of FIG. 4 for generating runner performance metric data in accordance with one embodiment. The baton device 102 includes an accelerometer 76, gyroscope 56, magnetometers 58 and heat rate monitor 57. In block 502, the method 500 may calculate total meters or distance. In block 504, the method may calculate total number of footsteps of the runner during a relay race phase coordinator 306. The distance provides the ability to analyze technical mechanics at any distance and/or running phase (i.e., Drive, Maximum Velocity, and Maintenance). The number of footsteps provides precise footstep data used to calculate stride length.

In block 506, the method 500 may calculate number of strides per minute, in block 508, calculate speed and in block 510, calculate pace. The optimal stride rate may be between 170 and 190 steps per minute. The stride rate provides precise data to employ strategies to adjust the turnover/stride rate (SR) in relation to gaining or decreasing speed at select running phases (i.e., higher and lower SR, respectively) ideally when analyzing exchange zone and curve running. The speed is calculated in relation to distance covered per second. The speed provides precise speed data for accurate placement of the "Go" mark tape for outgoing runners in exchange zones.

"Go" Mark

The area where the baton is passed is made up of a 20-meter to 30-meter exchange zone. Athletes and coaches are required to determine the ideal exchange zone spot for the outgoing runner to receive the baton at top speed. Savvy coaches and athletes use the formula distance=speed×time (d=s×t), then convert meters to feet in order to determine the outgoing runner's acceleration starting/static mark on the track (i.e., placement of "Go" mark).

Marking it off may be performed before a race or training. The outgoing runner marks with tape a spot about 6 meters to 9 meters before the exchange zone. When the incoming runner crosses that mark, the outgoing runner takes off. This approach requires precise variables and often is miscalculated. The training method is time-consuming as runners must perform multiple run-throughs to identify all variables to execute the ideal exchange zone spot. The baton device 102 captures all the required data points, and software/algorithms are used to do the calculations based on real-time metrics. The system 100 fully automates determining accurate "Go" marks. Any marks may also be captured by the eyeware device 128.

The pace is calculated as seconds per meter in relation to time and distance covered. The pace may be used to determine a derived pace time verses a target pace time.

In block 512, the method 500 may detect and/or analyze the heart rate. A heart rate monitor 57 detects the change in heartbeats through pulse/blood flow using optical sensing, for example. The heart rate may be analyzed to determine how the body is reacting to activity intensity. The heart rate may be used to determine composure or a poise factor.

Data may be presented by comparing athlete variations for: 1) male versus female athletes; 2) youth, high school, collegiate, and elite athletes; and 3) sprint, middle distance, and long-distance athletes.

By way of non-limiting example, at block 512, the heart rate analysis may be performed using an optoelectronic biometric module (OEBM) 316.

FIG. 6 illustrates a flowchart of a method 600 for determining the running economy with baton metrics, of block 404 of FIG. 4, by the relay race phase coordinator in accordance with one embodiment. In block 602, the method 600 may measure pitch of baton device 102. In block 604, the method may measure yaw of baton device 102. In block 606, the method 600 may measure roll of baton device 102. In block 608, the method 600 may measure motion in x, y, z axes of baton device 102. In block 610, the method may measure acceleration, angular velocity, and orientation. In block 612, the method may determine a baton swing deviation. In block 614, the method 600 may calculate average number of baton device strokes per meter. The measurement of blocks 602, 604, 606, 608 and 610 are measured by the motion sensor components. The motion sensor components include the magnetometer 58, the 3-axis accelerometer 76, and the 3-axis gyroscope 56. The 3-axis accelerometer 76 configured to sense acceleration/g-forces. The gyroscope 56 senses the tilt/angular momentum used to detect movement.

The baton swing deviation may determine the inferential drag (air resistance) effect on the baton device 102. The baton swing deviation is measured by the pitch, yaw and roll of the baton device 102 during the general running and the baton/hand impact point ±from baseline 0° or neutral.

The baton stokes rate may be used to determine the posture/running style with the baton device 102 and the impact on split time. The average number of baton strokes per meter at each baton device transition interval may be computed by the relay race training module 110.

FIG. 7 illustrates a flowchart of a method 700 for determining the running economy metrics associated with the Approach phase 308 of Table 3 in accordance with one embodiment. In block 702, the method 700 may determine the athlete is in an exchange zone.

There are various exchange zones in baton relay races, ranging from 20 meters to 30 meters long. The exchange zones start and end points are globally predetermined in meters by the track and field governing bodies (e.g., USATF, IAAF, NCAA, etc.). The commonly accepted parameters are a 6-meter to 9-meter "go" mark area, followed by a 20-meter to 30-meter exchange zone in sprint relays. Note that starting in 2018-19, the NCAA Playing Rules Oversight Panel and other track and field governing bodies approved expanding the "Exchange" zones to 30 meters in men's and women's track and field sprint relay races. Specifically, for the 4×100 meter relay, the 4×200 meter relay, and sprint medley relays, the first exchange zone will be 30 meters. Prior long-standing international track and field rules included a 10-meter acceleration area (also the "Fly Zone") followed by a 20-meter exchange zone (also the "International Zone").

The baton is programmed to incorporate all the exchange zone standards, and also allows for any rules or regulation updates via firmware. The baton's technology accumulates total distance in meters; thus, the supporting software/algorithms can perform exchange zone calculations (i.e., "go" mark and "exchange zone").

4×100 Meters Relay Example

Users use the GUI menu on the baton device or the mobile app to select the applicable event for race or training (i.e., 4×100, 4×400, etc.) to ensure proper calculations for the exchange zone start/end in meters.

To ensure accurate calculations, for each race or training session, users must reset the baton multi-user timer and all metrics to zero which is confirmed by the baton's speaker (i.e., speaker/microphone 48). For example, the user simultaneously holds the capacitive sensors located on both ends of the hollow cylindrical baton device for a predetermined time for timing reset.

| Runner | Exchange Zone | "Go" Mark Distance (6-9 m) | Exchange Zone Distance (30 m) |
|---|---|---|---|
| First Leg (Starting Line - 0 m) | NA | Start - 0 m | NA |
| Second Leg | Zone 1 | Start - 71 m to 74 m End - 80 m | Start - 80 m End - 110 m |
| Third Leg | Zone 2 | Start - 171 m to 174 m End - 180 m | Start - 180 m End - 210 m |
| Fourth Leg (Finish Line - 400 m) | Zone 3 | Start - 271 m to 274 m End - 280 m | Start - 280 m End - 310 m |

In block 704, the method 700 may calculate a baton device velocity rate of change in the exchange zone. The velocity rate of change is calculated within the exchange zone (acceleration/deceleration). An Incoming Runner must be within the 30-meter exchange zone for baton transition and baton take-over. An Outgoing Runner must be within the 30-meter exchange zone for baton transition and baton take-over. The velocity rate provides the intensity level at different running phases (i.e., Drive, Maximum Velocity, and Maintenance). The velocity rate may determine the inferential fatigue and speed endurance impact (e.g., "hitting the wall" due to glycogen and/or lactic acid effects). An example of a track and field baton relay with mark offs, an exchange zone, incoming runner, and outgoing runner is illustrated and described in "THE FASTEST BATON TO THE FINISH LINE," copyright 2012, by The New York Times Company, which is incorporated herein by reference in full. (archive.nytimes.com/www.nytimes.com/interactive/2012/07/23/sports/olympics/the-fastest-baton-to-the-finish-line.html).

Example running phases may include: 1) Drive Phase; 2) Maximum Velocity Phase; and 3) Maintenance Phase. Users use the GUI menu on the baton device 102 or the mobile application of the relay race training module 110 to select the applicable event for a race or training (i.e., 4×100, 4×400, etc.) to ensure proper analysis.

Rank Ordering for Relay Team

Example for 4×100 relay may define a $1^{st}$ Leg, a $2^{nd}$ Leg, $3^{rd}$ Leg and a $4^{th}$ Leg of a race. These legs may vary based on the type of relay race. The ranking order module 336 may rank the athletes based on the metrics from using baton device 102 to rank a list of athlete candidates 338 that would be best for one or more of the $1^{st}$ Leg, a $2^{nd}$ Leg, $3^{rd}$ Leg and $4^{th}$ Leg, for example, of a race. The applications 136 may include a GUI that displays that ranking order of the athlete candidates for forming a team. If a team requires more than four athletes, for example, the applications 136 may include a list of athlete candidates greater than four. The applications 136 may rank the athlete candidates based on each Leg of a race. Some candidates may overlap Legs, but a coach may select a particular one candidate for a Leg and then re-order the candidates, after a selection is made. Re-ordering may remove a selected candidate of one Leg from other Legs that has not yet assigned an athlete. Athletes may use the ranking order module 336 to find their own ranking order or to work with a group of athletes without a coach to assign athletes to Legs of a race.

The $1^{st}$ Leg (explosive runner) may be a Drive Phase that will use speed and distance metrics to rank an athlete. The Rank orders which runner accelerates the fastest in the first 10-20 meters.

The 2nd Leg (longest distance) may be a Maximum Velocity Phase that uses speed, distance and touch metrics to rank an athlete. The Rank orders which runner maintains a top-end speed the longest has a shortest use of exchange zone (efficiency/percentage) and effectively receives/passes the baton, which requires good "Baton Handoff" and "Transition" phase metrics.

The $3^{rd}$ Leg (most difficult leg/turn or curve specialist/shortest distance) may be a Drive Phase that uses a Stride Rate/Turnover and touch metrics to rank an athlete. The Rank orders which runner optimizes quickest/shortest stride for curve running and effectively receives/passes the baton associated with optimal "Baton Handoff and Transition" metrics.

The $4^{th}$ Leg (fastest runner) may be a Maintenance Phase that uses speed, Baton Stroke Rate, and Heart Rate metrics to rank an athlete. The Rank orders which runner can seamlessly shift speeds to catch or hold off other runners has a higher baton stroke rate which is indicative of short distance high-speed running; has good sprint posture in final meters to the finish line; and meets a certain heart rate metric (intensity and composure factor) or heart rate range.

In block 706, the method 700 may measure distance of usage efficiency in the exchange zone. The usage efficiency measures the distance usage within a 30-meter exchange zone as a function of total meters at each baton's transition interval. The length of the exchange zone is defined as the zone total meters (ZTM). The usage efficiency is defined by equation Eq(1):

Usage Efficiency=(Baton Total Meters (BTM)−Zone Meters Start (ZMS)/Zone Total Meters (ZTM) =Zone Efficiency (ZE).

For example, for first two zones of a 4×100: Zone 1 (103 m−80 m/30 m=76% ZE); and Zone 2 (207 m−180 m/30 m=90% ZE). In Zone 1, BTM=103 m, ZMS=80 m, and ZTM=30 m. In Zone 2, the BTM=207 m, ZMS=180 m, and ZTM=30 m. The ZMS may be determined based on end points of a zone.

The usage efficiency can be used to determine top-end speed point and provides distance strategy for each relay leg. Parameters are adjusted for each type of relay race—4×100, 4×200, 4×400, 4×800, Sprint/Distance Medleys, etc.

FIGS. 8A and 8B illustrate a flowchart of a method for proximity determination and the baton transition metrics associated with the Transition phase in accordance with one embodiment.

In block 802, the method 800 may determine an impact angle of the baton device 102. In block 804, the method 800 may determine an impact location (top, mid, bottom).

Baton Top End Determination (Incoming Runner)

The impact angle is measured by the hand touch point location on the baton using the capacitive sensors. For example, if the opposite end of the baton registers more untouched sensors, then this represents that the opposite end of the baton is the top end. If there are equal touch sensors at both ends of the baton, then this represents holding the baton at the mid-point. This also is used to identify the outgoing runner's hand impact location.

Baton Impact Location (Outgoing Runner)

The baton impact location is determined based on the hand positioning of the incoming runner as described above. Specifically, the outgoing runner's impact location is in relation to the hand positioning of the incoming runner. A secondary method (crosscheck) is to concurrently use the proximity touch sensor. This determines the location of both hands on the baton when the incoming and outgoing runner simultaneously touch the baton at the point of baton impact/handoff. This uses the automated track baton "Biometric Sensor-Switching Concept" where the capacitive sensors detect any change in the baton's baseline level of capacitance upon each hand contact.

There virtually are unlimited baton touch point locations. The reason being is that hypothetically, the entire baton surface operates as a tubular/cylinder touchscreen with accuracy >99% similar to cell phones or smartphones. The baton's entire inner surface is fitted with capacitive sensors constructed of transparent conductive materials, such as Indium Tin Oxide (ITO), a polyester (PET) film layer, or a glass substrate. The touch point/impact location represents the change in capacitance which can be measured by the microprocessor, proximity detector switch, and touch sensor controller and then converted to detect touch.

In block 806, the method 800 may determine a take-over time.

Proximity Determination Steps

The baton take-over time determination may be triggered by simultaneous hand touches by both runners, and then the baton motions are analyzed once solely in the hand of the outgoing runner.

At block 808, in FIG. 8B, the method 800 may determine if a baton take-over has been detected. If the determination at block 808 is "NO," the method process returns to wait for the detection of the baton take-over. If the determination at block 808 is "YES," the method 800 may proceed to block 810.

At block 810, the method 800 may determine a Handoff Method/Baton Impact Angel. The baton handoff method is determined based on the baton impact angle: a) Push-in (90°); b) Overhand Pass (<90° but usually around 30° to 60°); and 3) Upsweep (around 180°).

At block 812, the method 800 may determine the Baton Swing Deviation of Outgoing Runner. This is a change impact. Based on the angle determination in block 810, the relay race training module 110 determines the magnitude of the arm swing change in degrees and/or swing distance before the outgoing runner gets into their continuous running motion. Meaning, there is a longer arm swing motion for a fully extended straighten arm (Push-in Exchange; at shoulder height), compared to an arm closer to the body (Upsweep Exchange; closer to the hip/buttocks).

At block 814, the method 800 may determine proximity. The relay race training module 110 will be pre-programmed to correlate these data points, and translate/transform them to predetermined baton hand off methods and proximity distances aligned with relay exchange techniques, coaches' strategies, pros/cons, etc. Examples of handoff exchanges are described below.

Example, Push-in exchange, Upsweep exchange and Overhand pass exchange between runners are illustrated and described in "THE FASTEST BATON TO THE FINISH LINE," copyright 2012, by The New York Times Company, which is incorporated herein by reference in full. (archive-.nytimes.com/www.nytimes.com/interactive/2012/07/23/sports/olympics/the-fastest-baton-to-the-finish-line.html).

The Push-in exchange there is approximately a right angle or 90° such that the palm of the receiving runner faces toward the incoming runner. The incoming runner holds the baton device 102 vertically. The Upsweep exchange has a reflex angle of 270°-359°. During the Upsweep exchange, the palm of the receiving runner is facing down. The incoming runner positions the baton device 102 between the thumb and fingers of the receiving runner. The Overhand pass exchange has an acute angle less than 90°. The Overhand pass exchange is accomplished when the receiving runner has their palm facing up and the incoming runner passes the baton device 102 by placing it in the palm.

Example

Push-In Exchange (Low Risk)—Goal (double arm's length): Impact Angle—90° (Push-In Exchange)=Arm Angle Translation—around 180° (Safest Proximity Distance/Slowest Exchange Timing)

Overhand Pass Exchange (Moderate Risk)—Goal: Impact Angle—30° to 60° (Overhand Pass Exchange)=Arm Angle Translation—181° to 359° (Good Proximity Distance/Fast Exchange Timing)

Upsweep Exchange (High Risk)—Goal: Impact Angle—around 180° (Upsweep Exchange)=Arm Angle Translation—181° to 359° (Closest Proximity Distance/Fastest Exchange Timing)

FIG. 9 illustrates a flowchart of a method 900 for measuring the handoff body mechanics in accordance with one embodiment. In block 902, the method 900 may detect arm metric(s). In block 904, the method 900 may detect forearm metric(s). In block 906, the method 900 may detect wrist metric(s). In block 908, the method 900 may detect finger metric(s). Table 4 above describes the body mechanics during the Handoff phase 310. Using the capacitive sensors, the system determines the spreading or closing of fingers by calculating the number of simultaneous touch points via mutual capacitance technology, for example.

The handoff body mechanics are analyzed to determine if the outgoing runner provides a good hand target for an incoming runner based on the number of node touch points. For example, a goal may be five fingers contact with finger/thumb spread 6 to 10 inches. Capacitive sensors represent touch sensitive surfaces which are constructed of transparent conductive materials, such as Indium Tin Oxide (ITO), a polyester (PET) film layer, or a glass substrate.

The capacitive sensors may use projected capacitive technology which is made up of a matrix of rows and columns of conductive material, etched on a single conductive layer to form a grid pattern of electrodes. The capacitive sensors of the baton device 102 may detect touch by measuring the change of capacitance at an addressable electrode. Thus, the baton device 102 operates as a capacitance touch switch device that needs only one electrode to function. The electrode can be placed behind a non-conductive panel such as wood, glass, or plastic.

An electrode is an electrical conductor used to make contact with a nonmetallic part of a circuit or object. Electrodes are used with accuracy >99% similar to cell phones or smartphones. This change in capacitance can be measured by the microprocessor, proximity detector switch, and touch sensor controller and then converted to detect touch.

Figure 10:
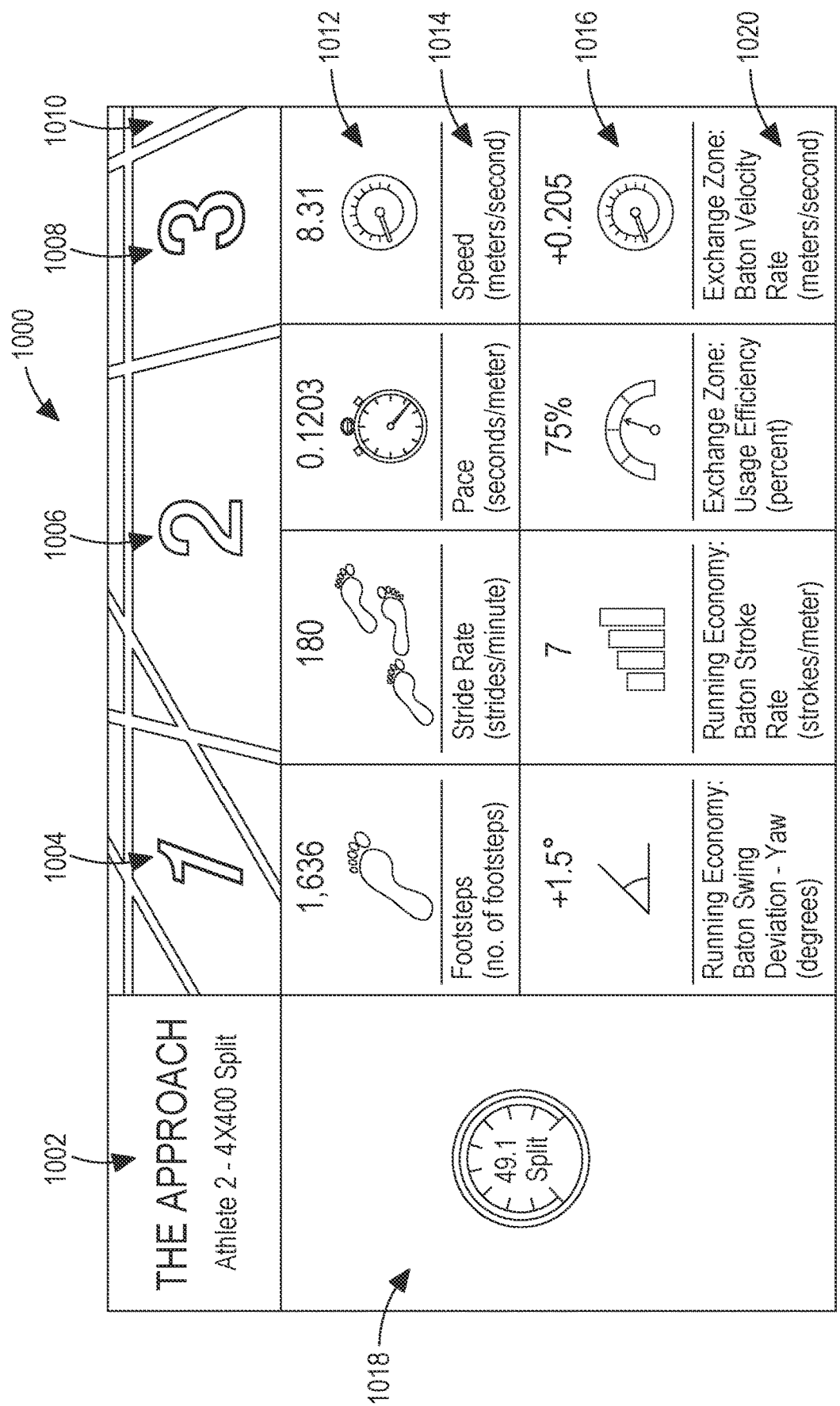
FIG. 10 illustrates a graphical user interface (GUI) of an Approach phase of an athlete in accordance with one embodiment.

FIG. 10 illustrates graphical user interface (GUI) 1000 of an Approach phase 308 of an athlete in accordance with one embodiment. The Approach phase GUI 1000 may include a plurality of columns and at least one row. Each column represents a metric of the approach phase. Various metrics of the approach phase 308 are also shown in FIG. 5.

The GUI 1000 may include in column 1002, an indicator of which athlete of the set of athletes of a relay race team is being displayed on a display device. The GUI 1000 may include a columns 1004, 1006, 1008 and 1010 and row 1018. Row 1018 includes sub-rows 1012, 1014, and 1016. The GUI 1000 may include in column 1002, row 1018, an icon of a meter for a split time of a corresponding one athlete. For example, in column 1004, sub-row 1012, the GUI 1000 may display a numerical representation of the number of footsteps, such as calculated at 504 of FIG. 5, together with an icon of a footprint. In column 1004, sub-row 1014, the GUI 1000 may display an explanation of the field in sub-row 1012 of column 1004. In column 1004, sub-row 1016, the GUI 1000 may display a numerical representation of a running economy metric associated with the baton swing deviations in degrees, such as calculated at 612 of FIG. 6, together with a graphical representation of the deviation angle. In column 1004, sub-row 1020, the GUI 1000 may display an explanation of the field in sub-row 1016 of column 1004.

In column 1006, sub-row 1012, the GUI 1000 may display the stride rate of the athlete, such as calculated at 506 of FIG. 5, together with an icon of multiple footprints. In column 1006, sub-row 1014, the GUI 1000 may display an explanation of the field in sub-row 1012 of column 1006. In column 1006, sub-row 1016, the GUI 1000 may display a numerical representation of a running economy metric associated with the baton stroke rate in strokes/meter, such as calculated at 614 of FIG. 6, together with a graphical representation of a bar graph. In column 1006, sub-row 1020, the GUI 1000 may display an explanation of the field in sub-row 1016 of column 1006.

In column 1008, sub-row 1012, the GUI 1000 may display a numerical value representative of the pace of the athlete, such as calculated at 510 of FIG. 5, together with an icon of a stopwatch. FIG. 14, as will be described in more detail, provides a GUI 1400 for an athlete's pace calculator. In column 1008, sub-row 1014, the GUI 1000 may display an explanation of the field in sub-row 1012 of column 1008. In column 1008, sub-row 1016, the GUI 1000 may display a numerical representation of an exchange zone metric associated with usage efficiency in percent, such as calculated at 706 of FIG. 7, together with a graphical representation of a gauge display. In column 1008, sub-row 1020, the GUI 1000 may display an explanation of the field in sub-row 1016 of column 1008.

Figure 13:
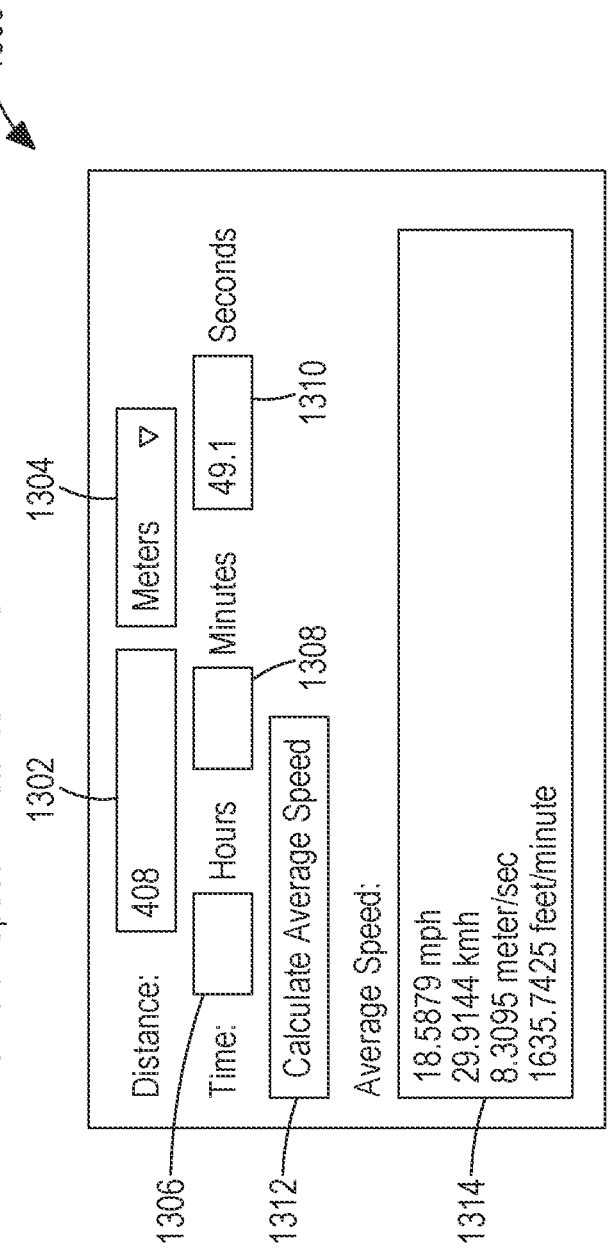
FIG. 13 illustrates a graphical user interface (GUI) of an average speed calculator for an athlete in accordance with one embodiment.

In column 1010, sub-row 1012, the GUI 1000 may display a numerical representation of the athlete's speed, such as calculated at 508 of FIG. 5, together with a gauge display of a speedometer. FIG. 13, as will be described in more detail, provides a GUI 1300 for an athlete's average speed calculator. In column 1010, sub-row 1014, the GUI 1000 may display an explanation of the field in sub-row 1012 of column 1010. In column 1010, sub-row 1016, the GUI 1000 may display a numerical representation of an exchange zone metric associated with the baton velocity rate in meters/second, such as calculated at 704 of FIG. 7, together with a graphical representation of a gauge display. In column 1010, sub-row 1020, the GUI 1000 may display an explanation of the field in sub-row 1016 of column 1010.

Figure 11:
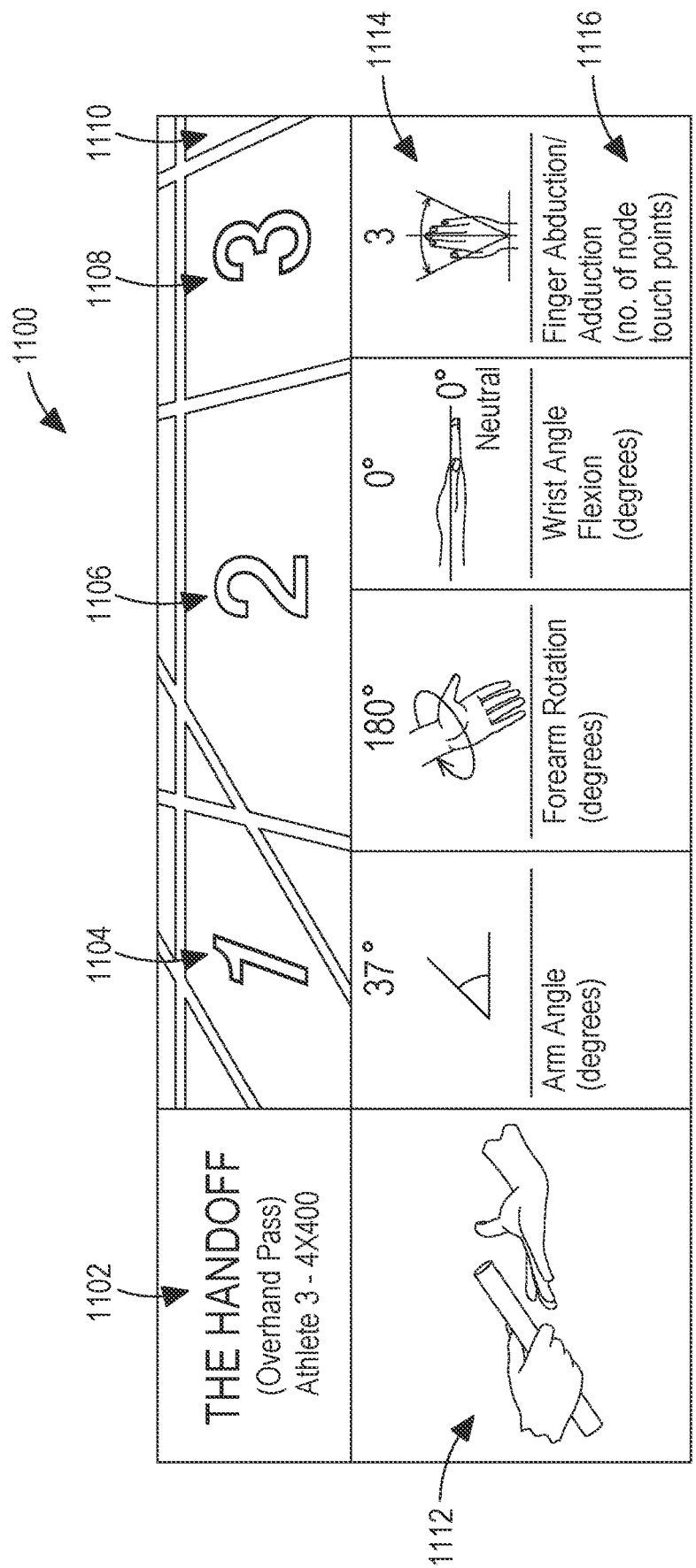
FIG. 11 illustrates a graphical user interface (GUI) of a Handoff phase of an athlete in accordance with one embodiment.

FIG. 11 illustrates a graphical user interface (GUI) 1100 of a Handoff phase of an athlete in accordance with one embodiment. The GUI 1100 includes columns 1102, 1104, 1106, 1108 and 1110 and row 1112. The column 1102, at row 1112, includes a field to display an icon of a handoff between runners using the baton device 102. Row 1112 includes two sub-rows, denoted as 1114 and 1116. The column 1104, at sub-row 1114, includes a field to display a numerical value, as determined at 902 of FIG. 9, and a graphical representation of a calculated arm angle in degrees. The column 1104, at sub-row 1116, includes an explanation of the column.

The column 1106, at sub-row 1114, includes a field to display a numerical value, as determined at 904 of FIG. 9, and an anatomical representation of a calculated forearm rotation in degrees. The column 1106, at sub-row 1116, includes an explanation of the column. The column 1108, at sub-row 1114, includes a field to display a numerical value as determined at 906 of FIG. 9, and an anatomical representation of a calculated wrist angle flexion in degrees. The column 1108, at sub-row 1116, includes an explanation of the column. The column 1110, at sub-row 1114, includes a field to display a numerical value, as determined at 908 of FIG. 9, and an anatomical representation of a calculated finger abduction/adduction based on the number of node touch points. The column 1110, at sub-row 1116, includes an explanation of the column.

Figure 12:
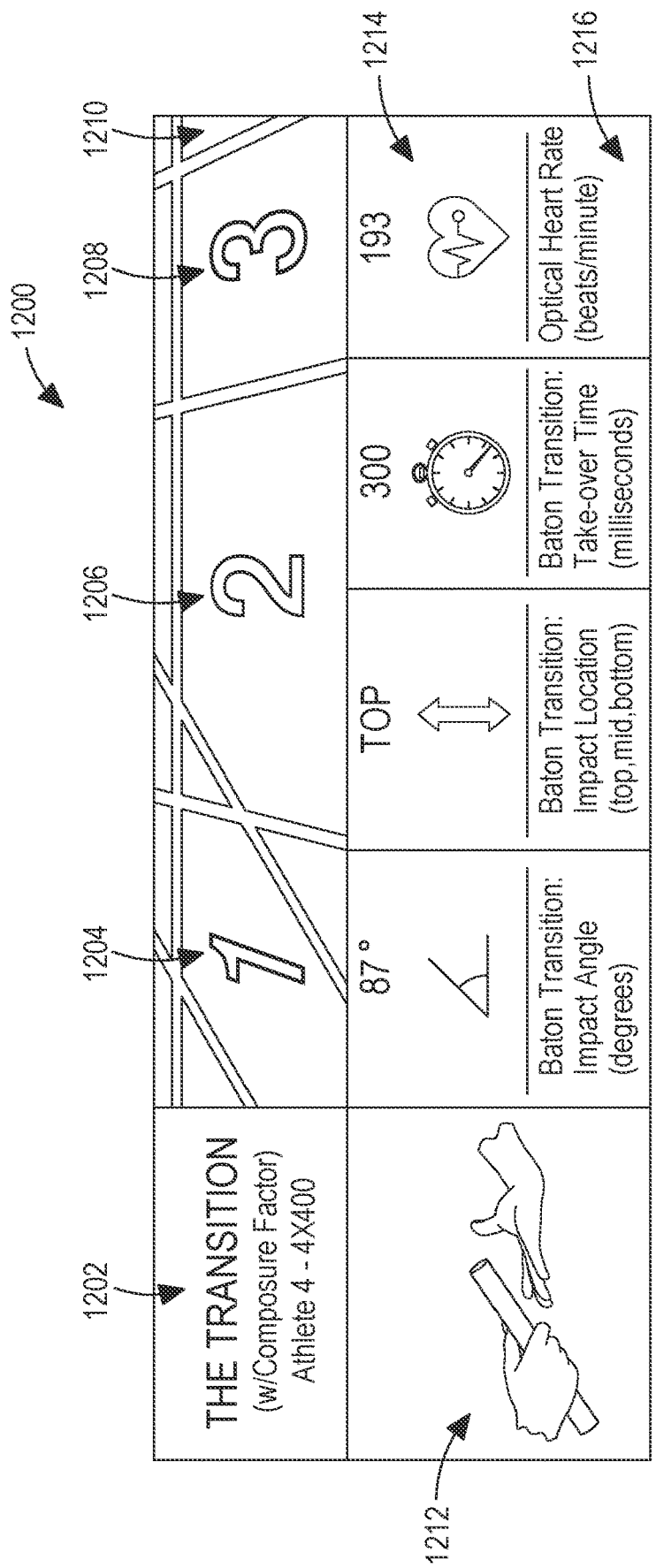
FIG. 12 illustrates a graphical user interface (GUI) of a Transition phase of an athlete in accordance with one embodiment.

FIG. 12 illustrates a graphical user interface (GUI) 1200 of a Transition phase of an athlete in accordance with one embodiment. The GUI 1200 includes columns 1202, 1204, 1206, 1208 and 1210 and row 1212. The row 1212 includes sub-rows 1214 and 1216.

The column 1204, at sub-row 1214 includes a field to display a numerical value, as determined at 802 in FIG. 8A, and a graphical representation of a baton transition impact angle in degrees. The column 1204, at sub-row 1216, includes an explanation of the column. The column 1206, at sub-row 1214, includes a field to display a numerical value, as determined at 804 in FIG. 8A, and a graphical representation of a baton transition impact location. The location may be one of Top, Mid and Bottom. The column 1206, at sub-row 1216, includes an explanation of the column.

The column 1208, at sub-row 1214, includes a field to display a numerical value and a graphical representation of baton transition take-over time in milliseconds, as determined at 806 in FIG. 8A. The column 1208, at sub-row 1216, includes an explanation of the column. The column 1210, at sub-row 1214, includes a field to display a numerical value of an optimal heart rate in beats/minute, as determined at 512 in FIG. 5, and a graphical representation of a heart. The column 1210, at sub-row 1216, includes an explanation of the column.

FIG. 13 illustrates a graphical user interface (GUI) 1300 of an average speed calculator for an athlete in accordance with one embodiment. The GUI 1300 includes a distance value field 1302 and a measurement unit field 1304, such as for the selection of meters, feet, or other measurements. In the example, the unit filed 1304 displays meters. The GUI 1300 may include one or more time value fields, such as hours 1306, minutes 1308 and seconds 1310. The GUI 1300 may include a display of calculation button 1312, such as "calculate average speed." For example, when a user clicks on the button 1312, the system receives such selection and calculates the average speed for the athlete. The GUI 1300 may include a display window 1314 which displays the calculated speed in various metric units, such as miles per hour (mph), kilometers per hour (kmh), meters per second and feet per minute, for example.

FIG. 14 illustrates a graphical user interface (GUI) 1400 of a pace calculator for an athlete in accordance with one embodiment. The GUI 1400 allows time, distance and/or pace of an athlete for an event to be determined based on information of the other two metrics. For example, if a user has values for distance and pace, the time can be calculated. If the user has values for time and pace, then the user can calculate the distance traveled by an athlete. Also, if the user has values for time and distance, the pace of an athlete can be calculated.

The GUI 1400 may include one or more time value fields, such as hours field 1402, minutes field 1404 and seconds field 1406, to input values, if known. The GUI 1400 may include a display of calculation button 1408, such as "calculate time" provided the distance and pace values are known. Once the system receives selection of button 1408, the time is calculated and displayed in fields 1402, 1404, and 1406.

The GUI 1400 includes a distance value field 1410 and a measurement unit field 1412, such as for the selection of meters, feet, or other measurements. In the example, the unit filed 1410 displays a meters unit. The GUI 1400 may include a "pick event" field 1414 with a drop-down box, for example. From the drop-down box, the user may select an event. In some embodiments, the system may store values. For example, distance values may be stored and automatically populated upon selecting an event from field 1414.

The GUI 1400 may include a display of calculate distance button 1416. For example, when a user clicks on the button 1416, the system receives such selection and calculates the distance traveled by the athlete, such as for a picked event shown in field 1414 or by calculating the distance based on the time and pace values.

The GUI 1400 may include one or more time value fields, such as hours 1418, minutes 1420 and seconds 1422. In the example, a unit filed 1424 is provided to display a selected distance unit. In this example, meters is displayed. The GUI 1400 may include a display of calculation button 1426, such as "calculate pace." For example, when a user clicks on the button 1426, the system receives such selection and calculates the pace for the athlete such as based on the time and distance values entered.

FIG. 15 illustrates a graphical user interface (GUI) 1500 of an acceleration calculator for an athlete in accordance with one embodiment. The GUI 1500 may include a description area 1502 describing principles of acceleration, for example, and an acceleration results field 1504.

The GUI 1500 includes field 1506 for an initial speed value, field 1510 for a final speed value, field 1514 for a time value. Field 1506 has a selectable unit field 1508 to select a measurement unit of speed, such as, mile/hour (mph).

The field 1510 has a selectable unit field 1512 to select a measurement unit of speed for the entered value, such as mile/hour (mph). The field 1514 may have a selectable unit field 1516 for selecting a measurement unit for time, such as seconds. The GUI 1500 may include a value field 1518 for the calculated acceleration. The value field 1518 and the numerical value in the results field 1504 are essentially the same for the selected measurement unit. The field 1518 may be updated for a selected measurement unit from field 1520. For example, the measurement unit may be meter/square section (m/s$^2$). Fields 1508, 1512, 1516 and 1520 when selected may display a drop-down box for available units.

Figure 16:
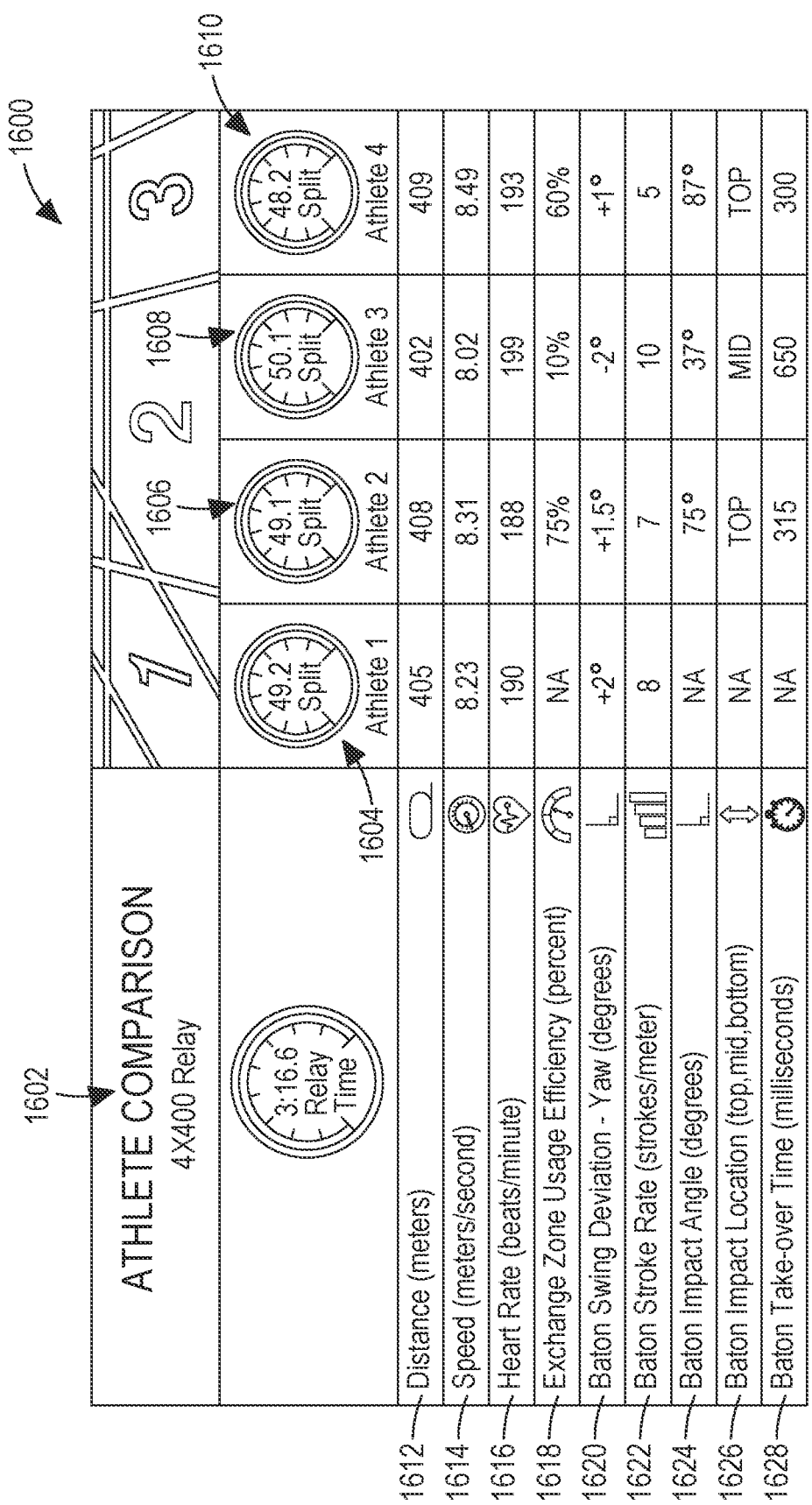
FIG. 16 illustrates a graphical user interface (GUI) of athlete comparisons in accordance with one embodiment.

FIG. 16 illustrates a graphical user interface (GUI) 1600 of athlete comparisons in accordance with one embodiment. The Athlete Comparison GUI 1600 may include a plurality of columns and rows. Each column 1604, 1606, 1608 and 1610 is designated for metrics of a respective one athlete of relay race team and uses a meter to display the athlete's split time, for example. This allows the metrics of all team members to be displayed side by side. Row 1612 displays the total race time in column 1602 in a meter icon.

Each row 1614, 1616, and 1618 displays a numerical value representative of a metric of the athlete's performance on a display device. The represented values are generated by the athlete performance model generator 302 of FIG. 3A. The metrics may include the distance in row 1614, speed in row 1616 and heart rate in row 1618. The distance, speed and heart rate are determined at blocks 502, 508 and 512, respectively, of FIG. 5.

The rows 1620, 1622, 1624, 1626 and 1628 display other metrics. Rows 1620 may display the exchange zone usage efficiency in percent of the Approach phase 308. Rows 1622 may display the baton swing deviation, as determined at block 612 of FIG. 6. This may be determined based on the 9 degrees of freedom. Row 1624 may display the calculated baton stroke rate (strokes/meter).

The baton stroke rate is a number that is related to the arm swing, speed, and stride. It also is aligned with the pedometer (footsteps) functionality. Below is scientific research and justification for this metric.

Kinematics

Human walking/running involves specific coordination patterns between upper and lower body segments which are dependent on walking/running speed.

Amplitude or frequency of arm movements is determined by the gait, meaning that the swing motion is adaptive to changing conditions. As the walking/running speed increases, the amplitude/frequency of the arm swing increases accordingly.

At speeds lower than approximately 0.8 meters per second (m/s), there is minimal arm swing, the arms move more or less in-phase, and the arm movement frequency is synchronized with the step frequency, resulting in a 2:1 frequency ratio between arm and leg movements.

At walking/running speeds higher than 0.8 meters per second (m/s), arm swing increases, the arms move out-of-phase, while the frequency of movement is synchronized with stride frequency, coinciding with a 1:1 frequency locking between arm and leg movements. Stride frequency is the number of steps taken in a given amount of time or over a given distance. This is sometimes referred to as cadence. For example, short quick strides (common with sprinters through 400 meters) increases stride frequency, but reduces stride length (M. P. Ford, R. C. Wagenaar, K. M. Newell (2007). Arm constraint and walking in healthy adults. Gait & Posture, 26, pg. 135-141.).

Baton Stroke Rate (Arm Swing Frequency and Stride Frequency)

The inventor adapted Arm Swing Frequency and Stride Frequency (footsteps/pedometer) to correlate/represent 1:1 for the baton stroke rate. An algorithm translates each start/stop end point of the arm swing (extension and flexion), where the flexion/frontal end point counts as one baton stroke. For example, one full arm swing counts as one baton stroke, whereas technically there are two arm swing end points, 1-front of body midpoint, then 1-rear of body midpoint. The motion sensors interprets/translates the baton's change in acceleration while in the runner's hand. This also directly aligns with the pedometer (footsteps) functionality. Simply, the algorithm interprets/translates the equivalent number of times the baton's pedometer counts one foot hitting the ground. Note that the baton strokes provided per the specification illustrations (Row 1624) are logical determination estimates based on the inventor's actual participation, coaching, and knowledge of the track and field sport. But the metric is continuously refined and validated with ongoing actual baton field and simulation testing.

Rows 1624, 1626 and 1628 may display a numerical value representative of the Transition phase 312. For example, row 1624 displays detected impact angle per athlete, as determined at block 802 of FIG. 8A. Row 1626 displays detected impact location per athlete, as determined at block 804 of FIG. 8A. Row 1628 displays the baton take-over time per athlete, as determined at block 806 of FIG. 8A. As should be understood, any metric determined in FIGS. 4-9 may be displayed in a GUI.

The example applies a projected baseline total relay time of 3:20.0. The 3:20.0 total time represents a baseline split equal to four runners @ 50.0 seconds each. The cumulative time of 3:16.6 is determined by using split time differentials (seconds) for each runner as applied to the predetermined baseline total relay time of 3:20.0.

The GUIs may allow a user to select a particular athlete's profile to obtain the metrics recorded for them during the race. The GUIs may be selective display based on user selection. One or more GUIs may be displayed simultaneously as window overlays and navigated using traditional navigational tools using icons and a mouse, a mouse wheel, keyboard arrow keys, or other keyboard control keys to move to and select the icons. For example, in a display device both one or more of the GUIs may be selectively displayed one at time or simultaneously, with one GUI overlaid over or partially over the other GUI. One or more GUIs may be displayed side by side, in some instances.

The tables above provide an explanation of benefits. A user may select a metric field from the GUI to display a benefit associated with the benefits as shown in Tables 1-5.

Figure 17:
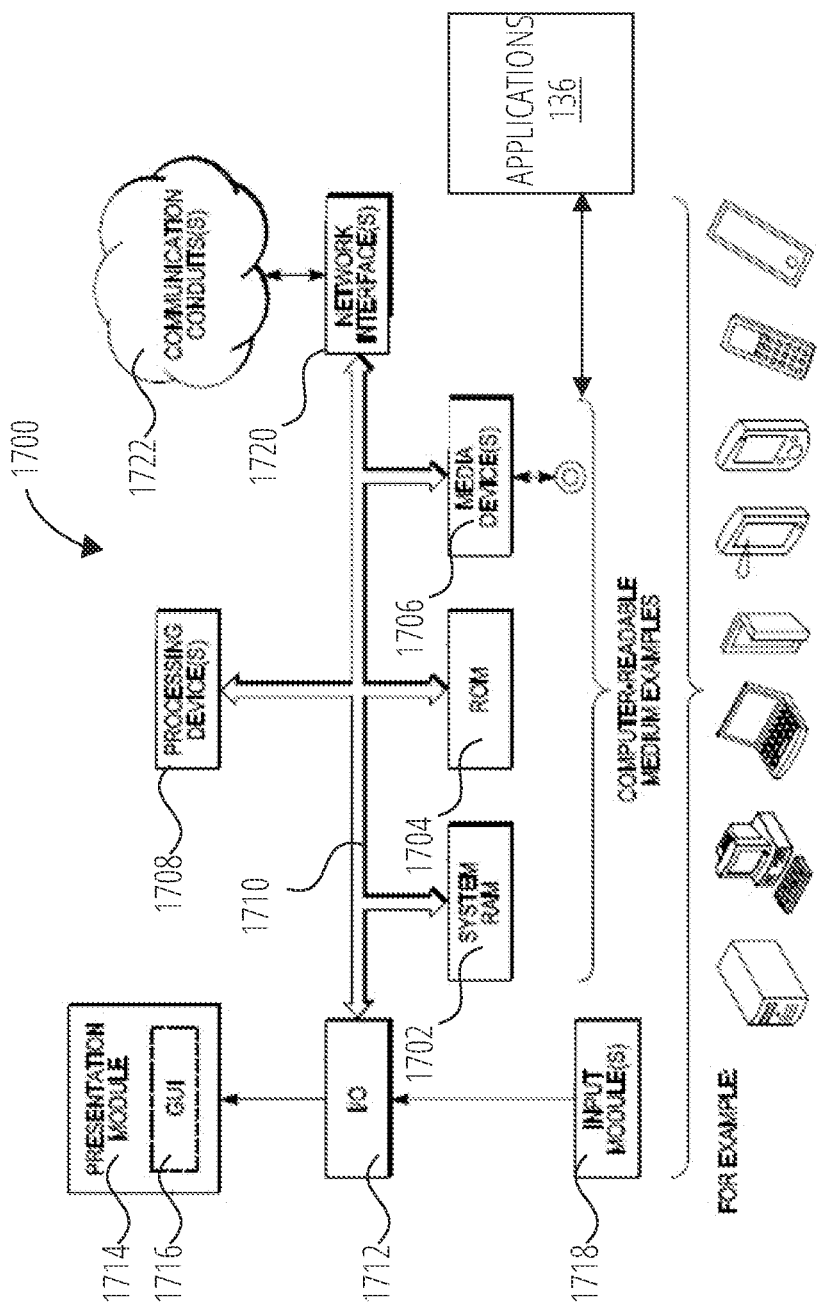
FIG. 17 illustrates block diagram of a computing device the subject matter in accordance with one embodiment.

Referring now to FIG. 17, in a basic configuration, a computing device 1700 (i.e., computing device 102) which may include any type of stationary computing device, server, cloud computing system, or a mobile computing device for tracking athlete performance and relay team performance. The eyeware device 128 may also use components of the computing device 1700. The computing device 1700 may include one or more processing devices 1706 and system memory in a hard drive. Depending on the exact configuration and type of computing device 1700, system memory may be volatile (such as RAM 1702), non-volatile (such as read only memory (ROM 1704), flash memory, and the like) or some combination of the two. A system memory may store an operating system, one or more applications, and may include program data providing the applications 136, machine learning, computer vision modules, and other algorithms as described herein.

The computing device 1700 may carry out one or more blocks/steps of a process described in relation to FIGS. 4-7, 8A and 8B. The computing device 1700 may also have additional features or functionality. As a non-limiting example, the computing device 1700 may also include additional data storage media devices 1708 (removable and/or non-removable) such as, for example, magnetic disks, optical disks, or tape. The computer storage media devices 1708 may include volatile and non-volatile, non-transitory, removable, and non-removable media implemented in any method or technology for storage of data, such as computer readable instructions, data structures, program modules or other data. The system memory, removable storage and non-removable storage are all non-limiting examples of computer storage media. The computer storage media may include, but is not limited to, RAM 1702, ROM 1704, Electrically Erasable Read-Only Memory (EEPROM), flash memory or other memory technology, compact-disc-read-only memory (CD-ROM), digital versatile disks (DVD) or other optical storage, magnetic cassettes, magnetic tape, magnetic disk storage or other magnetic storage devices, or any other physical medium which can be used to store the desired data and which can be accessed by computing device. Any such computer storage media may be part of device.

The computing device 1700 may also include or have input/output (I/O) interfaces 1712 for input modules 1718 such as a keyboard, mouse, pen, voice input device, touch input device, etc. The computing device may include or have I/O interfaces 1712 for connection to output device(s) such as a display, a presentation module 1714, speakers, etc. A graphical user interface (GUI) 1716 may be displayed on the presentation module 1714. The applications 136 may include user interfaces such as in the form of one or more GUIs to display athlete performance metrics and relay race phase metrics, coaching information, for example.

The computing device 1700 may include a peripheral bus 1710 for connecting to peripherals. Computing device 1700 may contain communication connection(s) that allow the device to communicate with other computing devices, such as over a network or a wireless network. By way of example, and not limitation, communication connection(s) may include wired media such as a wired network or direct-wired connection, and wireless media such as acoustic, radio frequency (RF), infrared and other wireless media. The computing device 1700 may include a network interfaces 1720, such as a network interface card to connect (wired or wireless) to a network or other communication conduits 1722.

Computer program code for carrying out operations described above may be written in a variety of programming languages, including but not limited to a high-level programming language, such as C or C++, Python, Java, for development convenience. In addition, computer program code for carrying out operations of embodiments described herein may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed Digital Signal Processor (DSP) or microcontroller. A code in which a program of the embodiments is described can be included as a firmware in a RAM, a ROM, and a flash memory. Otherwise, the code can be stored in a tangible computer-readable storage medium such as a magnetic tape, a flexible disc, a hard disc, a compact disc, a photo-magnetic disc, and a digital versatile disc (DVD).

The embodiments may be configured for use in a computer or a data processing apparatus which includes a memory, such as a central processing unit (CPU), a RAM and a ROM as well as a storage medium such as a hard disc.

The "step-by-step process" for performing the claimed functions herein is a specific algorithm, and may be shown as a mathematical formula, in the text of the specification as prose, and/or in a flowchart. The instructions of the software program create a special purpose machine for carrying out the particular algorithm. Thus, in any means-plus-function claim herein in which the disclosed structure is a computer, or microprocessor, programmed to carry out an algorithm, the disclosed structure is not the general-purpose computer, but rather the special purpose computer programmed to perform the disclosed algorithm.

A general-purpose computer, or microprocessor, may be programmed to carry out the algorithm/steps for creating a new machine. The general-purpose computer becomes a special purpose computer once it is programmed to perform particular functions pursuant to instructions from program software of the embodiments described herein. The instructions of the software program that carry out the algorithm/steps electrically change the general-purpose computer by creating electrical paths within the device. These electrical paths create a special purpose machine for carrying out the particular algorithm/steps.

"Communication media" typically comprise computer readable instructions, data structures, program modules, or other data in a modulated data signal, such as carrier wave or other transport mechanism. The communication media may also comprise any information delivery media. The term "modulated data signal" means a signal that has one or more of its characteristics set or changed in such a manner as to encode information in the signal. By way of example, and not limitation, communication media comprises wired media such as a wired network or direct-wired connection, and wireless media such as acoustic, infrared, and other wireless media. Combinations of any of the above are also included within the scope of computer readable medium.

Alternatively, or in addition, any of the functions described herein may be performed, at least in part, by one or more hardware logic components. For example, without limitation, illustrative types of hardware logic components that may be used include Field-programmable Gate Arrays (FPGAs), Application-specific Integrated Circuits (ASICs), Application-specific Standard Products, System-on-a-chip systems, Complex Programmable Logic Devices, and the like.

The terms "module" and "component" as used herein generally represent software, firmware, hardware, or combinations thereof. In the case of a software implementation, the module or component represents program code that performs specified tasks when executed on a processor. The program code may be stored in one or more computer readable memory devices, otherwise known as non-transitory devices. The features of the embodiments described herein are platform-independent, meaning that the techniques can be implemented on a variety of commercial computing platforms having a variety of processors (e.g., set-top box, desktop, laptop, notebook, tablet computer, personal digital assistant (PDA), mobile telephone, smart telephone, gaming console, wearable device, an Internet-of-Things device, and the like).

Unless otherwise defined, all terms (including technical and scientific terms) used herein have the same meaning as commonly understood by one of ordinary skill in the art to which embodiments belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In particular, unless specifically stated otherwise as apparent from the discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such data storage, transmission or display devices.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another. As used herein the expression "at least one of A and B," will be understood to mean only A, only B, or both A and B.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

Therefore, the breadth and scope of the subject matter provided herein should not be limited by any of the above explicitly described embodiments. Rather, the scope of the embodiments should be defined in accordance with the following claims and their equivalents.

What is claimed is:

1. A system comprising:
an electronic baton device comprising motion sensors and capacitive sensors;
a processor; and
non-tangible computer readable media having stored programming instructions thereon that, when executed, cause the processor to:
receive sensor data from the motion sensors and the capacitive sensors;
determine an exchange zone to exchange the electronic baton device between an incoming runner and an outgoing runner of a relay team of athletes, based on the received sensor data;
based on the received sensor data, determine relay race metrics for each athlete of the relay race team of athletes, baton metrics associated with said each athlete, a usage efficiency in the exchange zone, and baton transition metrics; and
selectively display on a display device the determined relay race metrics for each athlete, the determined baton metrics associated with said each athlete, the determined usage efficiency in the exchange zone, and the determined baton transition metrics in one or more selected graphical user interfaces.

2. The system of claim 1, wherein the programming instructions that, when executed, further cause the processor to:
detect arm metrics of the athlete while running with the baton device, based on the received sensor data;
detect wrist metrics of the athlete while running with the baton device, based on the received sensor data;
detect finger metrics of the athlete while running with the baton device that includes spreading or closing of fingers based on the athlete touching the capacitive sensors; and
selectively display on the display device the arm metrics, wrist metrics and finger metrics in the one or more selected graphical user interfaces.

3. The system of claim 2, wherein the programming instructions that, when executed, further cause the processor to, when detecting finger metrics, detect spreading or closing values of the fingers by calculating a number of simultaneous touch points associated with mutual capacitance of the capacitive sensors.

4. The system of claim 2, wherein the programming instructions that, when executed, further cause the processor to:
detect an impact angle per athlete based on the received sensor data;
detect an impact location per athlete based on athlete interaction with the capacitive sensors;
detect a baton take-over time per athlete based on the received sensor data; and
selectively display on the display device the impact angle, the impact location, and the baton take-over time in the one or more selected graphical user interfaces.

5. The system of claim 1, wherein the programming instructions that, when executed, further cause the processor to:
detect circumduction motions or movements based on the received sensor data.

6. The system of claim 1, wherein the programming instructions that, when executed, cause the processor to detect circumduction motions including programming instructions that, when executed, cause the processor to:
detect abduction/adduction based on the received sensor data;
detect elevation/depression based on the received sensor data;
detect flexion/extension based on the received sensor data; and
detect pronation/supination based on the received sensor data.

7. The system of claim 1, further comprising a mobile communication device, the mobile communication device comprising:
the processor;
the non-tangible computer readable media having the stored programming instructions;
the display device; and
communication hardware to collect the data from the motion sensors and the capacitive sensors.

8. The system of claim 1, wherein the programming instructions that, when executed, further cause the processor to:
detect posture/running style based on at least one of an angle between a forearm and an elbow of an arm and a stroke rate based on the received sensor data.

9. The system of claim 1, wherein the programming instructions that, when executed, further cause the processor to:
display side-by-side each athlete of the relay race team of athletes in a selected on graphical user interface.

10. The system of claim 1, wherein the programming instructions that, when executed, further cause the processor to:
determine when the incoming runner of the relay race team of athletes is within a 10-meter acceleration fly zone based on the received sensor data;
determine when the incoming runner of the relay race team of athletes is within a 20-meter to 30-meter exchange zone based on the received sensor data; and
determine when the outgoing runner of the relay race team of athletes is within the 20-meter to 30-meter exchange zone upon baton take-over based on the received sensor data.

11. A computer program product comprising:
one or more non-tangible and non-transitory computer readable media and programming instructions stored on the computer readable media, the programming instructions comprising:
program instructions to track and monitor performance of a relay race team of athletes during a relay race as each athlete interacts with an electronic baton device, wherein the electronic baton device includes motion sensors and capacitive sensors;
program instructions to collect sensor data from the motion sensors and the capacitive sensors;
program instructions to determine an exchange zone to exchange the electronic baton device between an incoming runner and an outgoing runner of a relay team of athletes based on the sensor data;
program instructions to, based on the collected sensor data, determine relay race metrics for each athlete of the relay race team of athletes, baton metrics associated with said each athlete, a usage efficiency in the exchange zone, and baton transition metrics; and
program instructions to selectively display on a display device the determined relay race metrics for each athlete, the determined baton metrics associated with said each athlete, the determined usage efficiency in the exchange zone, and the determined baton transition metrics in one or more selected graphical user interfaces.

12. The computer program product of claim 11, wherein: the programming instructions further include:
program instructions to detect arm metrics of the athlete while running with the baton device based on the collected sensor data;
program instructions to detect wrist metrics of the athlete while running with the baton device based on the collected sensor data;
program instructions to detect finger metrics of the athlete while running with the baton device that includes spreading or closing of fingers based on the athlete touching the capacitive sensors; and
program instructions to selectively display on the display device the arm metrics, wrist metrics and finger metrics in the one or more selected graphical user interfaces.

13. The computer program product of claim 12, wherein the programming instructions further include:
program instructions to, when detecting finger metrics, detect spreading or closing values of the fingers by calculating a number of simultaneous touch points associated with mutual capacitance of the capacitive sensors.

14. The computer program product of claim 12, wherein the programming instructions further include:
program instructions to detect an impact angle per athlete based on the collected sensor data;
programming instructions to detect an impact location per athlete based on an athlete's interaction with the capacitive sensors;
program instructions to detect a baton take-over time per athlete based on the collected sensor data; and
program instructions to selectively display on the display device the impact angle, the impact location, and the baton take-over time in the one or more selected graphical user interfaces.

15. The computer program product of claim 11, wherein the programming instructions further include:
program instructions to detect circumduction motions or movements based on the collected sensor data.

16. The computer program product of claim 15, wherein the program instructions to detect circumduction motions include:
program instructions to detect abduction/adduction based on the collected sensor data;
program instructions to detect elevation/depression based on the collected sensor data;
program instructions to detect flexion/extension based on the collected sensor data; and
program instructions to detect pronation/supination based on the collected sensor data.

17. The computer program product of claim 11, wherein the programming instructions further include:
program instructions to detect posture/running style based on at least one of an angle between a forearm and an elbow of an arm and a stroke rate, based on the collected sensor data.

18. The computer program product of claim 11, wherein the programming instructions, when selectively displaying on a display device the determined relay race metrics for each athlete in the one or more selected graphical user interfaces, further include:
program instructions to display side-by-side each athlete of the relay race team of athletes in a selected one graphical user interface.

19. The computer program product of claim 11, wherein the programming instructions further include:
program instructions to determine when the incoming runner of the relay race team of athletes is within a 10-meter acceleration fly zone based on the collected sensor data;
program instructions to determine when the incoming runner of the relay race team of athletes is within a 20-meter to 30-meter exchange zone based on the collected sensor data; and
program instructions to determine when the outgoing runner of the relay race team of athletes is within the 20-meter to 30-meter exchange zone upon baton takeover based on the collected sensor data.

20. A method, by a processor, comprising:
tracking and monitoring performance of a relay race team of athletes during a relay race as each athlete interacts with an electronic baton device, wherein the electronic baton device includes motion sensors and capacitive sensors;
collecting sensor data from the motion sensors and the capacitive sensors;
determining an exchange zone to exchange the electronic baton device between an incoming runner and an outgoing runner of a relay team of athletes based on the sensor data;
based on the collected sensor data, determining relay race metrics for each athlete of the relay race team of athletes, baton metrics associated with said each athlete, and usage efficiency in the exchange zone, and a baton transition metrics; and
selectively displaying on a display device, the determined relay race metrics for each athlete, the determined baton metrics associated with said each athlete, the determined usage efficiency in the exchange zone, and the determined baton transition metrics in one or more selected graphical user interfaces.

* * * * *